US012781270B2

(12) United States Patent
Kim et al.

(10) Patent No.: US 12,781,270 B2
(45) Date of Patent: Nov. 3, 2026

(54) METHOD FOR DETECTING A TARGET ANALYTE IN A SAMPLE USING AN S-SHAPED FUNCTION FOR A SLOPE DATA SET

(71) Applicant: SEEGENE, INC., Seoul (KR)

(72) Inventors: Hyo Jin Kim, Seoul (KR); Han Bit Lee, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 1407 days.

(21) Appl. No.: 17/311,723

(22) PCT Filed: Dec. 13, 2019

(86) PCT No.: PCT/KR2019/017733
§ 371 (c)(1),
(2) Date: Jun. 8, 2021

(87) PCT Pub. No.: WO2020/122679
PCT Pub. Date: Jun. 18, 2020

(65) Prior Publication Data

US 2022/0025449 A1 Jan. 27, 2022

(30) Foreign Application Priority Data

Dec. 14, 2018 (KR) ........................ 10-2018-0162444

(51) Int. Cl.
*G01N 33/48* (2006.01)
*C12Q 1/6851* (2018.01)

(52) U.S. Cl.
CPC .................................. *C12Q 1/6851* (2013.01)

(58) Field of Classification Search
None
See application file for complete search history.

(56) References Cited

U.S. PATENT DOCUMENTS

| | | | | |
|---|---|---|---|---|
| 6,303,305 | B1 | 10/2001 | Wittwer et al. | |
| 6,387,621 | B1 | 5/2002 | Wittwer | |
| 6,783,934 | B1 | 8/2004 | McMillan et al. | |
| 2002/0042051 | A1* | 4/2002 | Wittwer ............. | G01N 21/6428 536/23.1 |
| 2013/0273547 | A1* | 10/2013 | Li .......................... | G16B 25/00 435/6.12 |

FOREIGN PATENT DOCUMENTS

| | | | |
|---|---|---|---|
| EP | 1842924 | B1 | 6/2009 |
| WO | WO-2016/052991 | A1 | 4/2016 |
| WO | WO-2017/171469 | A1 | 10/2017 |
| WO | 2017/209563 | A1 | 12/2017 |

OTHER PUBLICATIONS

Zhao, Sheng, and Russell D. Fernald. “Comprehensive algorithm for quantitative real-time polymerase chain reaction.” Journal of computational biology 12.8 (2005): 1047-1064.*
International Search Report from corresponding PCT Application No. PCT/KR2019/017733, dated Apr. 13, 2020.
Rutledge, R. G. ‘Sigmoidal curve-fitting redefines quantitative real-time PCR with the prospective of developing automated high-throughput applications’, Nucleic acids research, 2004, vol. 32, No. 22, article No. e178, pp. 1-8.
Liu et al., Analytical Biochemistry 302, 52-59 (2002).
Tichopad et al., Biotechnology Letters 24: 2053-2056, 2002.
Ramakers et al., Neuroscience Letters 339 (2003) 62-66.
Peirson et al., Nucleic Acids Research, 2003, vol. 31, No. 14 e73.
Tichopad et al., Nucleic Acids Research, 2003, vol. 31, No. 20 e122.
Bar et al., Nucleic Acids Research, 2003, vol. 31, No. 17 e105.
Extended European Search Report from corresponding EP Application No. 19895176.6, dated Sep. 12, 2022.
Guescini et al., BMC Bioinformatics, vol. 9, No. 1, Jul. 30, 2008, p. 326.
Zhao Sheng et al. Journal of Computational Biology, vol. 12, No. 8, Oct. 1, 2005, pp. 1047-1064.

* cited by examiner

*Primary Examiner* — Anna Skibinsky
(74) *Attorney, Agent, or Firm* — Harness, Dickey & Pierce, P.L.C.

(57) ABSTRACT

The present invention relates to the detection of a target analyte in a sample using an S-shaped function for a slope data set. The method of the present invention comprises obtaining a first data set representing a growth curve by an amplification reaction for the target analyte; wherein said first data set includes a plurality of data points, each having a cycle number and a signal value at the cycle number; calculating a slope value at each cycle number for the first data set to obtain a second data set; wherein said second data set includes a plurality of data points, each having a cycle number and a slope value at the cycle number; calculating an S-shaped function that approximates a selected portion of the second data set; and using the S-shaped function to detect the target analyte in a sample.

14 Claims, 12 Drawing Sheets

Specification includes a Sequence Listing.

METHOD FOR DETECTING A TARGET ANALYTE IN A SAMPLE USING AN S-SHAPED FUNCTION FOR A SLOPE DATA SET

CROSS-REFERENCE TO RELATED APPLICATIONS

This application is a national phase application of PCT Application No. PCT/KR2019/017733 filed on 13 Dec. 2019, which claims the benefit of and priority to Korean Patent Application No. 10-2018-0162444 filed on 14 Dec. 2018. The entire disclosures of the applications identified in this paragraph are incorporated herein by references.

BACKGROUND OF THE INVENTION

Field of the Invention

The present invention relates to a method for detecting a target analyte in a sample using an S-shaped function for a slope data set.

Description of the Related Art

A polymerase chain reaction (hereinafter referred to as "PCR") which is most widely used for the nucleic acid amplification includes repeated cycles of denaturation of double-stranded DNA, followed by oligonucleotide primer annealing to the DNA template, and primer extension by a DNA polymerase (Mullis et al., U.S. Pat. Nos. 4,683,195, 4,683,202 and 4,800,159; Saiki et al., (1985) Science 230, 1350-1354).

A real-time PCR is one of PCR-based technologies for detecting a target analyte in a sample in a real-time manner. For detecting a certain target analyte, the real-time PCR employs a signal-generating means for capable of generating detectable fluorescence signals in a proportional manner with the amount of the target molecule. The generation of fluorescence signals may be accomplished by using either intercalators generating signals when intercalated between double-stranded DNA or oligonucleotides carrying fluorescent reporter and quencher molecules. The fluorescence signals whose intensities are proportional with the amount of the target molecule are detected at each amplification cycle and plotted against amplification cycles, thereby obtaining an amplification curve or amplification profile curve.

PCR amplification curves typically have multiple stages: a baseline phase in which fluorescence remains approximately constant, an exponential phase in which the fluorescence approximately doubles for each cycle, and a plateau phase as the amplification tapers off.

The baseline phase refers to a region in which there is little change in fluorescent signal during initial cycle of PCR. In the baseline region, the level of PCR amplicon is not sufficient to be detectable and therefore signals detected in this region may be due to background signal involving fluorescent signals from reaction reagents and measurement device. The exponential phase shows increase in fluorescent signals in proportional to increase of amplification products. The plateau phase refers to a region in which there is little increase in fluorescent signals due to saturation of both PCR amplicon and fluorescent signal levels.

To date, various methods have been developed to detect a target analyte in a sample using a data set obtained by real-time PCR.

One of the methods involves determining whether at least signal values exceed a predetermined threshold. It requires collecting many data sets to set a more suitable threshold value for each reaction. As an alternative, U.S. Pat. Nos. 6,303,305 and 6,783,934 disclose a method for determining as a threshold cycle (Ct) value an $n^{th}$ order derivative maximum of an amplification curve; Liu et al. discloses a method for determines as a Ct value a first derivative maximum of a sigmoid fitting model (Liu and Saint, 2002; Tichopad et al., 2002).

Further, a quantitative method using a standard curve is well known in the art. It uses serial dilutions of a known standard material to generate an amplification curve and plots log transformed concentrations of the standard material against Ct values to obtain a standard curve for quantification. Then, an unknown sample is quantified by calculating from the standard curve the concentration corresponding to the Ct value for the unknown sample.

As another method, a quantitative method using an internal control has been proposed.

Recently, approaches have been proposed to quantify target nucleic acids through mathematical modeling of amplification curves. Since the shape of the exponential curve of the raw PCR fluorescence data contains information about amplification efficiency, computing efficiency from the kinetics of individual PCR reaction is theoretically possible. Other methods include use of the amplification plot (Liu and Saint, 2002), the first derivative maximum of sigmoid model fitting (Liu and Saint, 2002; Tichopad et al., 2002), the interactive window-of-linearity algorithm (Ramakers et al., 2003), the mid-value point regression (Peirson et al., 2003), the studentized residual statistics followed by four-parameter logistic model fitting algorithm (FPLM) (Tichopad et al., 2003), and the kinetic outlier detection (KOD) method (Bar et al., 2003).

The aforementioned methods are focusing on using a data set obtained from a reaction such as a raw data set, either directly or by its mathematical modeling, for detecting a target analyte.

As an alternative approach, the present invention provides a novel method for detecting a target analyte using an S-shaped function for a slope data set.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop a novel method of processing a data set obtained from an amplification reaction for detection of a target analyte. As a result, we have found that a target analyte can be detected using an S-shaped function that approximates a selected portion of a slope data set.

Accordingly, it is an object of the present invention to provide a method for detecting a target analyte in a sample.

It is another object of this invention to provide a computer readable storage medium containing instructions to configure a processor to perform a method for detecting a target analyte in a sample.

It is still another object of this invention to provide a device for detecting a target analyte in a sample.

It is still another object of this invention to provide a computer program to be stored in a computer readable storage medium to configure a processor to perform a method for detecting a target analyte in a sample.

Other objects and advantages of the present invention will become apparent from the detailed description to follow taken in conjugation with the appended claims and drawings.

DETAILED DESCRIPTION OF THIS INVENTION

I. Detection of Target Analyte Using Slope Data Set

In one aspect of the present invention, there is provided a method for detecting a target analyte in a sample, comprising the steps of:

(a) obtaining a first data set representing a growth curve by an amplification reaction for a target analyte; wherein said first data set includes a plurality of data points, each having a cycle number and a signal value at the cycle number;

(b) calculating a slope value at each cycle number for the first data set to obtain a second data set; wherein said second data set includes a plurality of data points, each having a cycle number and a slope value at the cycle number;

(c) calculating an S-shaped function that approximates a selected portion of the second data set; and (d) using the S-shaped function to detect the target analyte in a sample.

The present inventors have made intensive researches to develop a novel method of processing a data set obtained from an amplification reaction for detection of a target analyte. As a result, we have found that a target analyte can be detected using an S-shaped function that approximates a selected portion of a slope data set.

Figure 1:
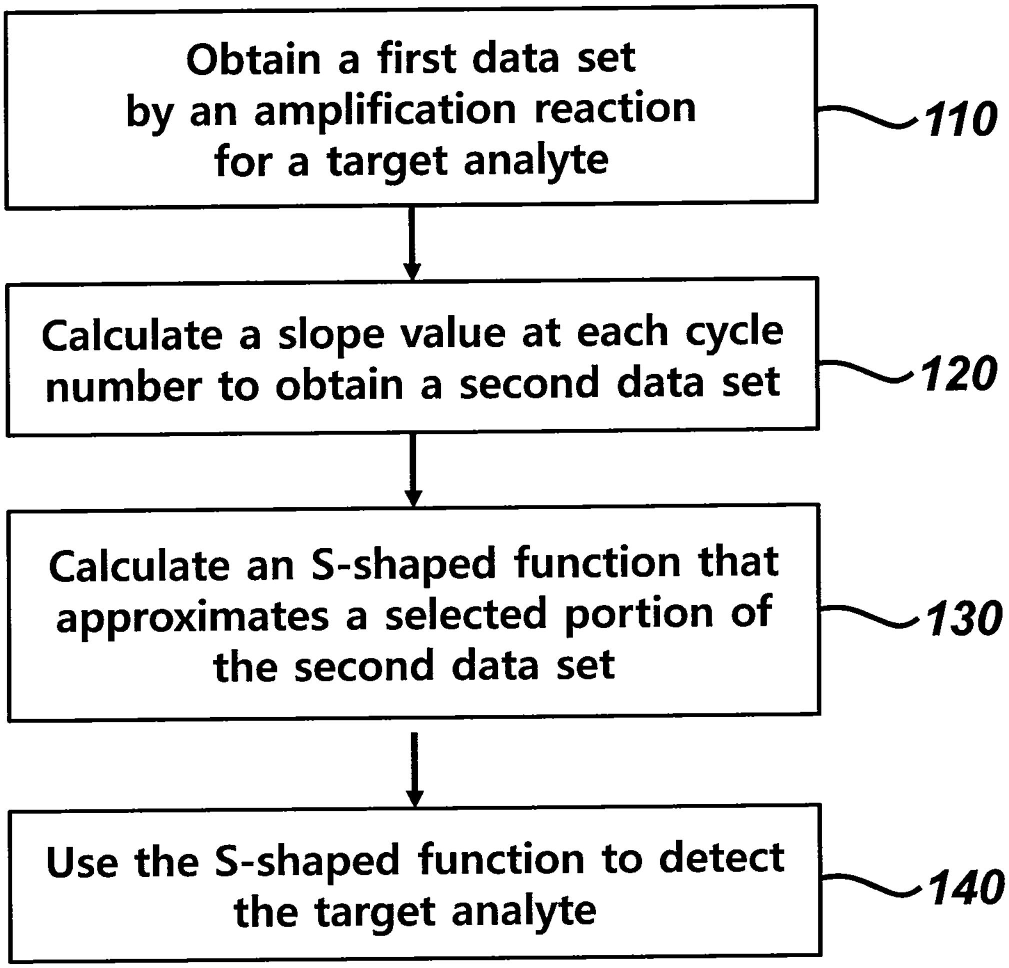
FIG. 1 is a flow chart illustrating a method in accordance with an embodiment of the present invention.

The detection of a target analyte in a sample in accordance with the method of the present invention is schematically illustrated in FIG. 1. The method of the present invention will be described in more detail as follows:

Step (a): Obtaining First Data Set for Target Analyte

According to the present invention, a first data set representing a growth curve is obtained by an amplification reaction for a target analyte (110). Said first data set includes a plurality of data points, each having a cycle number and a signal value at the cycle number.

The first data set as used herein may be used interchangeably with "amplification data set".

The term used herein "target analyte" may include various materials (e.g., biological materials and non-biological materials such as chemicals). Particularly, the target analyte may include biological materials such as nucleic acid molecules (e.g., DNA and RNA), proteins, peptides, carbohydrates, lipids, amino acids, biological chemicals, hormones, antibodies, antigens, metabolites and cells. More particularly, the target analyte may include nucleic acid molecules. According to an embodiment, the target analyte may be a target nucleic acid molecule. The target analyte is present in a sample.

The term "sample" as used herein refers to any material undergoing the method of the present invention. Particularly, the term "sample" refers to any material containing or presumed to contain a nucleic acid of interest or which is itself a nucleic acid containing or presumed to contain a target nucleic acid sequence of interest. More particularly, the term "sample" as used herein includes biological samples (e.g., cells, tissues, and fluid from a biological source) and non-biological samples (e.g., food, water and soil). The biological samples includes, but not limited to, virus, bacteria, tissue, cell, blood, serum, plasma, lymph, sputum, swab, aspirate, bronchoalveolar lavage fluid, milk, urine, feces, ocular fluid, saliva, semen, brain extracts, spinal cord fluid (SCF), appendix, spleen and tonsillar tissue extracts, amniotic fluid and ascitic fluid. In addition, the sample may include natural-occurring nucleic acid molecules isolated from biological sources and synthetic nucleic acid molecules.

The term used herein "target nucleic acid", "target nucleic acid sequence" or "target sequence" refers to a nucleic acid sequence of interest for analysis or detection. The target nucleic acid sequence comprises a sequence in a single strand as well as in a double strand. The target nucleic acid sequence comprises a sequence newly generated in reactions as well as a sequence initially present in a sample.

The target nucleic acid sequence may include any DNA (gDNA and cDNA), RNA molecules and their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature.

The target nucleic acid sequence should not be construed as limiting the sequence known at a given time or the sequence available as of a given time, but instead should be read to encompass the sequence that may be available or known now or at any time in the future. In other words, the target nucleic acid sequence may or may not be known at the time of practicing the present method. In case of unknown target nucleic acid, its sequence may be determined by one of conventional sequencing methods prior to performing the present method.

When a target analyte is a target nucleic acid molecule, the sample is subjected to a nucleic acid extraction process. The nucleic acid extraction process may vary depending on the type of sample. When the extracted nucleic acid is RNA, reverse transcription process is performed additionally to synthesize cDNA from the extracted RNA (Joseph Sambrook, et al., *Molecular Cloning, A Laboratory Manual*, Cold Spring Harbor Laboratory Press, Cold Spring Harbor, N.Y. (2001)).

According to an embodiment of this invention, the target nucleic acid sequences comprise a nucleotide variation.

The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term "nucleotide variation" used herein includes any variation at a particular location in a nucleic acid sequence. In other words, the term "nucleotide variation" includes a wild type and its any mutant type at a particular location in a nucleic acid sequence.

In an embodiment, the first data set used herein is obtained by a signal-generating process.

The term used herein "signal-generating process" refers to any process capable of generating signals in a dependent manner on a property of a target analyte in a sample, i.e., activity, amount or presence (or absence) of the target analyte, in particular the presence of (or the absence of) an analyte in a sample. The signal-generating processes herein include biological and chemical reactions. Such biological reactions include genetic analysis such as PCR, real-time PCR and microarray analysis, immunological analysis, and bacterial growth analysis. According to one embodiment, the signal-generating process comprises analyzing the production, change or destruction of a chemical.

The signal-generating process is accompanied with signal change. The signal change may serve as an indicator indicating qualitatively or quantitatively the presence or absence of a target nucleic acid sequence.

The details of "signal-generating process" are disclosed in WO 2015/147412 filed by the present inventors, the teachings of which are incorporated herein by reference in its entirety.

According to an embodiment, the signal-generating process is an amplification process, in particular a signal amplification process.

According to an embodiment of this invention, the signal-generating process is a process with or without amplification of a target analyte.

Particularly, the signal-generating process is a process with amplification of a target nucleic acid molecule. More particularly, the signal-generating process is a process with amplification of a target nucleic acid molecule and capable of increasing or decreasing signals (particularly, increasing signals) upon amplifying the target nucleic acid molecule.

The term used herein "signal generation" include appearance or disappearance of signals and increase or decrease in signals. Particularly, the term "signal generation" means increase in signals.

The signal-generating process may be performed in accordance with a multitude of methods known to one of skill in the art. Examples of such methods can be referred to in the following description of the signal generating means.

According to an embodiment, the signal-generating process is performed in a process involving signal amplification together with target amplification.

According to an embodiment, the amplification reaction as the signal-generating process is performed in such a manner that signals are amplified simultaneously with amplification of the target nucleic acid molecule (e.g., real-time PCR). Alternatively, the amplification reaction is performed in such a manner that signals are amplified with no amplification of the target nucleic acid molecule [e.g., CPT method (Duck P, et al., Biotechniques, 9:142-148 (1990)), Invader assay (U.S. Pat. Nos. 6,358,691 and 6,194, 149)].

A multitude of methods have been known for amplification of a target nucleic acid molecule, including, but not limited to, PCR (polymerase chain reaction), LCR (ligase chain reaction, see Wiedmann M, et al., "Ligase chain reaction (LCR)—overview and applications." PCR Methods and Applications 1994 February; 3(4):S51-64), GLCR (gap filling LCR, see WO 90/01069, EP 439182 and WO 93/00447), Q-beta (Q-beta replicase amplification, see Cahill P, et al., Clin Chem., 37(9):1482-5(1991), U.S. Pat. No. 5,556,751), SDA (strand displacement amplification, see G T Walker et al., Nucleic Acids Res. 20(7):16911696 (1992), EP 497272), NASBA (nucleic acid sequence-based amplification, see Compton, J. Nature 350(6313):912 (1991)), TMA (Transcription-Mediated Amplification, see Hofmann W P et al., J Clin Virol. 32(4):289-93(2005); U.S. Pat. No. 5,888,779) or RCA (Rolling Circle Amplification, see Hutchison C. A. et al., Proc. Natl Acad. Sci. USA. 102:1733217336(2005)).

The term "signal" as used herein refers to a measurable output. The term "signal value" as used herein is an expression indicating a signal in a quantitative manner.

The signal strength or signal change may serve as an indicator indicating qualitatively or quantitatively the presence or absence of an analyte (a target nucleic acid sequence).

Examples of useful indicators include fluorescence intensity, luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The signal change may include a signal decrease as well as a signal increase. According to an embodiment, the signal-generating process is a process of amplifying the signal values.

Signals include various signal characteristics from the signal detection, e.g., signal intensity [e.g., RFU (relative fluorescence unit) value or in the case of performing amplification, RFU values at a certain cycle, at selected cycles or at end-point], signal change shape (or pattern) or Ct value, or values obtained by mathematically processing the characteristics.

According to an embodiment, the term "signal" includes not only signals per se obtained at detection temperatures but also a modified signal provided by mathematically processing the signals.

According to an embodiment of this invention, when an amplification curve is obtained by real-time PCR, various signal values (or characteristics) from the amplification curve may be selected and used for determination of target presence (intensity, Ct value or amplification curve data).

The signal (particularly, the signal intensity) may vary depending upon its detection temperature as well as a signal-generating means employed.

The term used herein "signal-generating means" refers to any material used in the generation of a signal indicating a property, more specifically the presence or absence of the target analyte which is intended to be analyzed.

The term "signal-generating means" as used herein refers to any material used in generation of signals indicating the presence of target nucleic acid sequences, for example including oligonucleotides, labels and enzymes. Alternatively, the term "signal-generating means" as used herein can be used to refer to any methods using the materials for signal generation.

A wide variety of the signal-generating means have been known to one of skill in the art. The signal-generating means include both labels per se and oligonucleotides with labels. The labels may include a fluorescent label, a luminescent label, a chemiluminescent label, an electrochemical label and a metal label. The label per se may serve as signal-generating means, for example, an intercalating dye. Alternatively, a single label or an interactive dual label containing a donor molecule and an acceptor molecule may be used as signal-generating means in the form of linkage to at least one oligonucleotide. The signal-generating means may comprise additional components for generating signals such as nucleolytic enzymes (e.g., 5'-nucleases and 3'-nucleases).

The signal generating means can be classified based on their signal-generating modes, as follows:

a. Signal-generating means which generates a signal by the formation of a duplex between a target nucleic acid sequence and a detection oligonucleotide that specifically hybridizes to the target nucleic acid sequence.

As used herein, the term "detection oligonucleotide" is an oligonucleotide that is involved in the generation of a signal to be detected. According to one embodiment, the detection oligonucleotide comprises an oligonucleotide involved in the actual signal generation. For example, the signal generation depends on hybridization or non-hybridization of the detection oligonucleotide with another oligonucleotide (e.g., an oligonucleotide comprising a nucleotide sequence complementary to a target nucleic acid sequence or the detection oligonucleotide). According to one embodiment, the detection oligonucleotide comprises at least one label.

The signal generation by the formation of a duplex between the target nucleic add sequence and the detection oligonucleotide can be accomplished by various methods, including Scorpion method (Whitcombe et al., Nature Biotechnology 17:804-807(1999)), Sunrise or Amplifluor method (Nazarenko et al., Nucleic Acids Research, 25(12): 2516-2521(1997), and U.S. Pat. No. 6,117,635), Lux method (U.S. Pat. No. 7,537,886), Plexor method (Sherrill C B et al., Journal of the American Chemical Society, 126: 4550-4556 (2004)), Molecular Beacon method (Tyagi et al, Nature Biotechnology v. 14 Mar. 1996), HyBeacon method (French D J et al., Mol. Cell Probes, 15(6):363-374(2001)), adjacent hybridization probe method (Bernard, P. S. et al., Anal. Biochem., 273:221(1999)) and LNA method (U.S. Pat. No. 6,977,295).

b. Signal-generating means which generates a signal by the formation of a duplex in a dependent manner on cleavage of a mediation oligonucleotide specifically hybridized with a target nucleic acid sequence. The term "mediation oligonucleotide" as used herein refers to an oligonucleotide which mediates production of a duplex not containing the target nucleic acid sequence.

According to an embodiment, the cleavage of the mediation oligonucleotide per se does not generate signal and a fragment formed by the cleavage is involved in successive reactions for signal generation.

The signal generation by the duplex formed in a dependent manner on cleavage of the mediation oligonucleotide can be accomplished by various known methods, including PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (WO 2014/104818).

c. Signal-generating means which generates a signal by hybridization of the detection oligonucleotide to a target nucleic add sequence, followed by cleavage of the detection oligonucleotide. The signal generation by hybridization of the detection oligonucleotide with the target nucleic acid sequence and then cleavage of the detection oligonucleotide can be accomplished by various methods, including TaqMan probe method (U.S. Pat. Nos. 5,210,015 and 5,538,848).

d. Signal-generating means which generates a signal by cleavage of the detection oligonucleotide in a dependent manner on cleavage of the mediation oligonucleotide specifically hybridized to the target nucleic acid sequence.

According to one embodiment, where the mediation oligonucleotide hybridized to the target nucleic acid sequence is cleaved to release the fragment, the fragment specifically hybridizes to the detection oligonucleotide and induces cleavage of the detection oligonucleotide.

The signal generation by cleavage of the detection oligonucleotide in a dependent manner on cleavage of the mediation oligonucleotide can be accomplished by various known methods, including Invader assay (U.S. Pat. Nos. 5,691,142, 6,358,691 and 6,194,149), PCEC (PTO Cleavage and Extension-Dependent Cleavage) method (WO 2012/134195) and a method described in U.S. Pat. No. 7,309,573.

The term "signal amplification reaction" as used herein refers to a reaction for increasing or decreasing signals generated by a signal-generating means.

According to an embodiment, the signal amplification reaction refers to an increase (or amplification) of a signal generated depending on the presence of the target analyte by using the signal-generating means. The signal amplification reaction is accompanied with or without an amplification of the target analyte (e.g., nucleic add molecule). More particularly, the signal amplification reaction refers to a signal amplification accompanied with an amplification of the target analyte.

The first data set obtained by the signal amplification reaction comprises cycle numbers.

The term used herein "cycle number" or "cycle" refers to a unit of changes of conditions in a plurality of measurements accompanied with changes of conditions. For example, the changes of conditions include changes in temperature, reaction time, reaction number, concentration, pH and/or replication number of a target nucleic acid molecule sequence. Therefore, the cycle may include time or process cycle, unit operation cycle and reproductive cycle.

As an example, when enzyme kinetics is investigated, the reaction rate of an enzyme is measured several times as the concentration of a substrate is increased regularly. In this reaction, the increase in the substrate concentration may correspond to the changes of the conditions and the increasing unit of the substrate concentration may be corresponding to a cycle.

As another example, an isothermal amplification allows for a plurality of measurements for a sample in the course of reaction time under isothermal conditions and the reaction time may correspond to the changes of conditions and a unit of the reaction time may correspond to a cycle. For example, where a 5 minute interval such as 5, 10, 15 minutes, etc. is set to one reaction time, the cycle may be expressed as a 5-minute cycle, 10-minute cycle, 15-minute cycle, or the like. Alternatively, considering the 5-minute interval as one unit, the 5-minute cycle can be represented by $1^{st}$ cycle, the 10-minute cycle by $2^{nd}$ cycle, the 15-minute cycle by $3^{rd}$ cycle, and the like.

As another example, for a melting analysis or a hybridization analysis, a change in a signal may be measured while changing a temperature within a range of temperatures and the temperature may correspond to the changes of conditions and a unit of the temperature (e.g., measurement temperature) may correspond to a cycle. For example, where a 0.5° C. interval such as 40° C., 40.5° C., 50° C., 50.5° C., etc. is set to one reaction time, the cycle may be expressed as a 40° C.-cycle, 40.5° C.-cycle, 50° C.-cycle, 50.5° C.-cycle, or the like. Alternatively, considering the 0.5° C. interval as one unit, the 40° C.-cycle can be represented by $1^{st}$ cycle, the 40.5° C.-cycle by $2^{nd}$ cycle, a 50° C.-cycle by $3^{rd}$ cycle, or the like.

Particularly, when repeating a series of reactions or repeating a reaction with a time interval, the term "cycle" refers to a unit of the repetition.

For example, in a polymerase chain reaction (PCR), a cycle refers to a reaction unit comprising denaturation of a target molecule, annealing (hybridization) between the target molecule and primers and primer extension. The increases in the repetition of reactions may correspond to the changes of conditions and a unit of the repetition may correspond to a cycle.

The first data set obtained by an amplification reaction includes a plurality of data points, each having a cycle number and a signal value at the cycle number.

The term "signal value" as used herein means either a numerical value of the signal level (e.g., signal intensities) actually measured at each cycle of the signal-generating process or its modification. The modification may include mathematically processed value of measured signal value. Examples of a mathematically processed value of a measured signal value (i.e., a signal value in a raw data set) may include a value obtained by addition, subtraction, multiplication, or division, or a logarithmic value.

The term "data point" as used herein means a coordinate value comprising a cycle and a signal value at the cycle. The term "data" as used herein means any information comprised in a data set. For example, cycles and signal values of an amplification reaction are data, respectively.

The data points obtained from a signal-generating reaction, particularly from a signal amplification reaction, may be plotted with coordinate values in a rectangular coordinate system. In the rectangular coordinate system, the X-axis represents cycles of the amplification reaction and the Y-axis represents signal values measured at each cycles or their modifications.

The term "data set" as used herein refers to a set of data points. For example, the data set may include a raw data set which is a set of data points obtained directly from the amplification reaction using a signal-generating means. Alternatively, the data set may be a modified data set which is obtained by a modification of the data set including a set of data points obtained directly from the signal-generating process. The data set may include an entire or a partial set of data points obtained from the signal-generating process or modified data points thereof. The data set comprises a plurality of data points. The data set may comprise at least 2 data points. Particularly, the number of data points in the data set may be at least 2, 3, 4, 5, 10 or 20. The number of data points in the data set may be not more than 1000 data points. Particularly, the number of data points in the data set may be not more than 1000, 500, 300, 200, 100, 90, 80, 70 or 60. The number of data points in a data set may be 3-1000. Particularly, the number of data points in the data set may be 3-1000, 10-500, 1-100, 20-100, 20-80, 20-70 or 20-60. According to an embodiment, the number of data points in the data set may be 20-60.

In an embodiment, the first data set may be obtained by processing a plurality of data sets. Where two target analytes are detected in a single reaction, a data set for each of the two target analytes may be provided by processing data sets obtained by the single reaction. For example, a data set for each of the two target analytes may be provided by measuring signals at two different temperatures to obtain two data sets and processing the two data sets.

The first data set may be plotted to give an amplification curve.

According to one embodiment of the invention, the amplification curve is one obtained by the amplification reaction of the target analyte (specifically, a target nucleic acid molecule).

In an embodiment, the first data set of step (a) of the present invention is a raw data set, a mathematically modified data set of the raw data set, a normalized data set of the raw data set, or a normalized data set of the mathematically modified data set.

In a particular embodiment of the invention, the first data set of step (a) is a raw data set. As used herein, the term "raw data set" refers to a data set comprising signals obtained directly from a signal-generating reaction. For example, a raw data set includes a set of signals which are obtained from a signal receiving device, subjected to basic signal processing on a collecting device, and then passed to a signal analyzing step.

In a particular embodiment of the invention, the first data set of step (a) is a mathematically modified data set of the raw data set. The term "mathematically processed data set" as used herein refers to a data set that has been modified through mathematical processing from a raw data set. The mathematically modified data set is a baseline subtracted data set obtained by removing a background signal value from the raw data set. The baseline subtracted data set may be obtained by methods well known in the art (e.g., U.S. Pat. No. 8,560,240).

In one embodiment of the invention, the first data set of step (a) is a normalized data set of the raw data set or a normalized data set of the mathematically modified data set. The term "normalization" as used herein refers to a process for reducing or eliminating a signal variation between data sets for a plurality of reactions. The term "calibration" or "adjustment" as used herein refers to correcting or modifying data (particularly, signal values) of a data set for analytical purposes. The normalization is one aspect of the calibration.

According to an embodiment, the normalized data set may be provided by a method comprising the steps of:

(i) providing a normalization coefficient for calibrating the raw data set or the mathematically modified data set of the raw data set; wherein the data set is provided from signals generated by a signal-generating reaction using a signal-generating means; wherein the data set includes a plurality of data points, each having a cycle number and a signal value at the cycle number; wherein the normalization coefficient is provided by using a reference value, a reference cycle and the data set; wherein the reference value is an arbitrarily determined value; wherein the normalization coefficient is provided by defining a relationship between the reference value and a signal value at a cycle of the data set corresponding to the reference cycle; and (ii) providing a normalized data set by obtaining calibrated signal values by applying the normalization coefficient to the signal values of the data set.

The reference cycle is a cycle selected for determining a specific signal value used for providing a normalization coefficient with a reference value. The reference cycle used for providing a normalization coefficient may be selected arbitrarily from cycles of the data set.

According to an embodiment, the reference cycle may be selected from the cycles in a background region.

The background signal is a signal generated by an analytical system itself, or by the signal-generating means itself not involved in the target analyte, not by a target analyte in a sample. The background region is a region in which only a background signal is generated and the signal due to a target analyte rarely occurs.

The background region refers to an early stage of a signal-generating process before amplification of signal is sufficiently detected. Specifically, the reference cycle may be determined from the cycles 1-30, 2-30, 2-20, 2-15, 2-10, 2-8, 3-30, 3-20, 3-15, 3-10, 3-9, 3-8, 4-8, or 5-8 in the background region.

A reference value is a value used for providing a normalization coefficient. A reference value of the present invention refers to an arbitrary value that is applied to a reference cycle for the calibrations of signal values of a data set. A reference value may be an arbitrarily determined value. Preferably, the reference value may be an arbitrarily determined value from a real number except zero. Preferably, a reference value may be the same-typed value as the values of a data set to be calibrated and may have the same unit or dimension as the data set to be calibrated.

When the normalization coefficient is provided by a reference value and a signal value at the reference cycle-corresponding cycle of the data set, the normalization coefficient may be provided by a ratio of the signal values at the reference cycle-corresponding cycle of the data set to the reference value.

Step (b): Obtaining a Second Data Set

Afterwards, a slope value is calculated at each cycle number for the first data set to obtain a second data set. Said second data set includes a plurality of data points, each having a cycle number and a slope value at the cycle number.

The second data set as used herein may be used interchangeably with "slope data set".

The term "slope value" as used herein refers to a change in signal value at each data point, and which may be used interchangeably with "change value". The slope value or change value may encompass a change ratio, and thus the slope data set may encompass a change ratio data set.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

The slope value may be obtained by a method known in the art, including, but not limited to, a differentiation, a difference, a difference quotient, a ratio, or linear regression analysis of the signal values.

The calculation of the slope value by a differentiation generally involves calculating a function that approximates the first data set (e.g., a raw data set), calculating a derivative function from the approximated function, and then obtaining a slope value at each cycle number using the derivative function.

The calculation of the slope value by a difference generally involves calculating a difference between a signal value at a cycle number at which the slope value is to be calculated (target signal value) and a signal value at another cycle number (reference signal value), and taking the difference as a slope value at the target cycle number. The reference signal value may be, for example, a signal value at a cycle number immediately before or immediately after the target cycle number, or may be a signal value at a cycle number at two or more cycles before or after the target cycle number. Alternatively, the reference signal value may be an average of the signal values at several cycle numbers before or after the target cycle number. Typically, the reference signal value may be a signal value at the cycle number immediately before the target cycle number.

The calculation of the slope value by a difference quotient generally involves calculating the difference between a signal value at a cycle number at which the slope value is to be calculated (target signal value) and a signal value at another cycle number (reference signal value), dividing the calculated difference by the difference between the target cycle number and the reference cycle number, and taking the resultant as a slope value at the target cycle. The reference signal value may be, for example, a signal value at a cycle number immediately before or immediately after the target cycle number, or may be a signal value at a cycle number at two or more cycles before or after the target cycle number. The slope value determined by the difference quotient corresponds to the change amount of the signal value per cycle number.

The calculation of the slope value by a ratio generally involves calculating a ratio between two signal values at two cycle numbers. In an embodiment, the ratio at a target cycle number is calculated by dividing a signal value at the target cycle by a signal value at an immediately preceding cycle.

The calculation of the slope vale by linear regression analysis generally involves obtaining a linear function that fits several data points including the data point at which the slope value is to be calculated (target data point) and determining the increase amount of the signal value per cycle number in the fitted function. The number of the data points used for obtaining the linear function may be two or more data points, for example, not more than 2, 3, 4, 5, 6, 7, 8, 9, 10, 11, 12, 13, 14 or 15.

Examples of the linear regression analysis includes, but not limited to, a least square method.

The least square method may be represented by Equation I below:

Equation I $$m = \frac{\sum_{i=I-a}^{I+b}(x_i - \overline{x})(y_i - \overline{y})}{\sum_{i=I-a}^{I+b}(x_i - \overline{x})^2}$$

$$\overline{x} = \frac{\sum_{i=I-a}^{I+b} x_i}{n},\ \overline{y} = \frac{\sum_{i=I-a}^{I+b} y_i}{n}$$

wherein

I is a cycle of a data point at which slope is to be calculated, m is a slope of a data point at $I^{th}$ cycle, $x_i$ is a cycle of $j^{th}$ cycle, $y_j$ is a signal value measured at $i^{th}$ cycle, $S_i$ is a slope value at $i^{th}$ cycle.

The "n" or "a+b+1" is the number of data points used for calculating a slope at $I^{th}$ cycle, called as LSMR (Linear Squares Method Range). The "a" is a value for calculating a minimum cycle among a set of data points used for calculating a slope at $I^{th}$ cycle. The "b" is a value for calculating a maximum cycle. The "a" and "b" independently represent an integer of 0-10, particularly 1-5, more particularly 1-3. Although it is advantageous that the values of "a" and "b" are the same, they may be different from each other depending on the subject of measurement, the measurement environments and the cycle at which the slope is to be measured.

According to an embodiment, the calculation of the slope value at a certain cycle number(s) may differ from that at the remaining cycle numbers. For example, where slope values are obtained by a difference method, a slope value at a first cycle number or an end cycle number may be obtained by other methods than the difference method; where slope values are obtained by linear regression analysis, slope values at initial cycle numbers (e.g., the first cycle number and second cycle numbers) or late cycle numbers (e.g., the end cycle number and immediately preceding cycle number) may be obtained by other methods than the linear regression analysis.

For example, a slope value at a first cycle number or an end cycle number may be determined as zero (0). Alternatively, a slope value at a first cycle number may be determined as a signal value at the first cycle number or second cycle number. Alternatively, a slope value at a first cycle number or an end cycle number may be determined as a predetermined value.

According to one embodiment, the method may further comprise correcting slope values of one or more data points in the slope data set, between steps (a) and (c).

Examples of such correction include correcting abnormal signals in the slope data set, which involves detection of a cycle number having an abnormal signal value in the slope data set and then correction of the slope value corresponding to the abnormal cycle number detected.

Step (c): Calculation of an S-Shaped Function that Approximates a Selected Portion of the Second Data Set Next, an S-shaped function that approximates a selected portion of the second data set is calculated.

The present inventors have found that a certain portion of the second data set exhibits a pattern of an amplification curve or growth curve associated with the presence of the target analyte. Based on this finding, the present invention suggests that an S-shaped function which approximates a selected portion of the second data set can be used for detection or quantification of the target analyte.

According to the present invention, the step (c) may comprise the following sub-steps:

(c1) selecting a portion which exhibits a pattern of an amplification curve or growth curve in the slope data set and which can be fitted to an S-shaped function such as a sigmoid function; and (c2) calculating an S-shaped function such as a sigmoid function that approximates the selected portion.

In one embodiment, the selected portion in the second data set (slope data set) of step (c) is a cycle region exhibiting a pattern of an amplification curve or growth curve in the presence of the target analyte. In other words, the selected portion may be within a cycle region exhibiting a pattern of an amplification curve or growth curve in the presence of the target analyte.

In one embodiment, the selected portion in the second data set (slope data set) of step (c) is a cycle region exhibiting a pattern in which the slope value increases with cycle number in the presence of the target analyte. In other words, the selected portion may be within a cycle region exhibiting a pattern in which the slope value increases with cycle number in the presence of the target analyte.

Typically, a slope data set such as the second data set represents a "bell-shaped curve" known as the normal distribution in the presence of the target analyte. The left side of the bell-shaped curve with respect to the axis of symmetry (central axis) shows an increasing pattern like an amplification curve or growth curve, that is, a pattern in which a slope value increases as the cycle number increases, whereas the right side of the bell-shaped curve shows a pattern in which a slope value decreases as the cycle number increases. Thus, the left side in a slope data set representing a bell-shaped normal distribution may be selected as the "portion" to be approximated by an S-shaped function according to the method of the present invention.

In one embodiment, the selected portion in the second data set of step (c) is within a range of a first cycle number to a cycle number having a maximum slope value in the second data set. As described above, since the maximum slope value is at the axis of symmetry in the slope data set representing the bell-shaped normal distribution, the upper limit of the end cycle of the selected portion may be defined by the axis of symmetry in the slope data set.

The start cycle and the end cycle defining the metes and bounds of the selected portion in the second data set of step (c) are as follows:

(i) Start Cycle

The start cycle of the selected portion may be selected in consideration of goodness of fit of the S-shaped function that approximates or fits the selected portion.

In one embodiment, the start cycle of the selected portion is any one of $1^{st}$ to $30^{th}$ cycle numbers; any one of $1^{st}$ to $25^{th}$ cycle numbers; any one of $1^{st}$ to $20^{th}$ cycle numbers; any one of $1^{st}$ to $15^{th}$ cycle numbers; any one of $1^{st}$ to $10^{th}$ cycle numbers; or any one of $1^{st}$ to $5^{th}$ cycle numbers in the second data set.

In a particular embodiment, the start cycle of the selected portion is any one of $1^{st}$ to $10^{th}$ cycle numbers in the second data set.

In another embodiment, the start cycle of the selected portion may be any one of $2^{nd}$ to $30^{th}$ cycle numbers; any one of $2^{nd}$ to $25^{th}$ cycle numbers; any one of $2^{nd}$ to $20^{th}$ cycle numbers; any one of $2^{nd}$ to $15^{th}$ cycle numbers; any one of $2^{nd}$ to $10^{th}$ cycle numbers; any one of $2^{nd}$ to $5^{th}$ cycle numbers; any one of $3^{rd}$ to $30^{th}$ cycle numbers; any one of $3^{rd}$ to $25^{th}$ cycle numbers; any one of $3^{rd}$ to $20^{th}$ cycle numbers; any one of $3^{rd}$ to $15^{th}$ cycle numbers; any one of $3^{rd}$ to $10^{th}$ cycle numbers; any one of $3^{rd}$ to $5^{th}$ cycle numbers; any one of $4^{th}$ to $30^{th}$ cycle numbers; any one of $4^{th}$ to $25^{th}$ cycle numbers; any one of $4^{th}$ to $20^{th}$ cycle numbers; any one of $4^{th}$ to $15^{th}$ cycle numbers; any one of $4^{th}$ to $10^{th}$ cycle numbers; any one of $4^{th}$ to $5^{th}$ cycle numbers in the second data set. The slope value at initial cycle numbers, such as the first, second, or third cycle number, in the second data set tends to include noise that is not derived from the target analyte. Therefore, it is desirable to ensure that such initial cycle numbers are not included in the selected portion to increase the goodness of fit of the function.

In another embodiment, the start cycle is selected from at least 5 consecutive cycle numbers immediately before an end cycle number; at least 7 consecutive cycle numbers immediately before an end cycle number; at least 10 consecutive cycle numbers immediately before an end cycle number; at least 20 consecutive cycle numbers immediately before an end cycle number; at least 25 consecutive cycle numbers immediately before an end cycle number; at least 30 consecutive cycle numbers immediately before an end cycle number; at least 35 consecutive cycle numbers immediately before an end cycle number; or at least 40 consecutive cycle numbers immediately before an end cycle number in the second data set.

In a particular embodiment, the start cycle of the selected portion may be selected from the 3-$10^{th}$ cycle numbers in the second data set.

(ii) End Cycle

The end cycle of the selected portion may be selected in consideration of goodness of fit of an S-shaped function that approximates or fits the selected portion.

As described above, for a slope data set such as the second data set representing the bell-shaped normal distribution, a portion after a cycle number having a maximum slope value exhibits a pattern in which a slope value decreases as the cycle number increases, that is, a pattern like a non-amplification curve or a non-growth curve. Including data points after the cycle number having a maximum slope value into the selected portion may worsen goodness of fit of an S-shaped function such as a sigmoid function. Therefore, it is preferable to exclude data points after the cycle number having a maximum slope value from the selected portion of step (b).

In one embodiment, the end cycle of the selected portion is a cycle number having a maximum slope value or any of fifteen (15) consecutive cycle numbers immediately before the cycle number having a maximum slope value in the second data set; a cycle number having a maximum slope value or any of ten (10) consecutive cycle numbers immediately before the cycle number having a maximum slope value in the second data set; a cycle number having a maximum slope value or any of seven (7) consecutive cycle numbers immediately before the cycle number having a maximum slope value in the second data set; a cycle number having a maximum slope value or any of six (6) consecutive cycle numbers immediately before the cycle number having a maximum slope value in the second data set; a cycle number having a maximum slope value or any of five (5) consecutive cycle numbers immediately before the cycle number having a maximum slope value in the second data set; a cycle number having a maximum slope value or any of four (4) consecutive cycle numbers immediately before the cycle number having a maximum slope value in the second data set; a cycle number having a maximum slope value or any of three (3) consecutive cycle numbers immediately before the cycle number having a maximum slope value in the second data set; a cycle number having a maximum slope value or any of two (2) consecutive cycle numbers immediately before the cycle number having a maximum slope value in the second data set; or a cycle number having a maximum slope value or a cycle number immediately before the cycle number having a maximum slope value in the second data set.

In a particular embodiment, the end cycle of the selected portion is a cycle number having a maximum slope value or any of five consecutive cycle numbers immediately before the cycle number having a maximum slope value in the second data set. Specifically, the end cycle of the selected portion is a cycle number having a maximum slope value; a cycle number at five cycles before the cycle number having a maximum slope value; a cycle number at four cycles before the cycle number having a maximum slope value; a cycle number at three cycles before the cycle number having a maximum slope value; a cycle number at two cycles before the cycle number having a maximum slope value; or a cycle number at a cycle before the cycle number having a maximum slope value. For example, if the cycle number having the maximum slope value in the slope data set is $35^{th}$ cycle number, the end cycle of the selected portion is $35^{th}$ cycle number, $34^{th}$ cycle number, $33^{rd}$ cycle number, $32^{nd}$ cycle number, $31^{st}$ cycle number, or $30^{th}$ cycle number in the second data set.

In one embodiment, the end cycle of the selected portion is a cycle number having a maximum slope value in the second data set. For example, if the cycle number having the maximum slope value in the slope data set is $35^{th}$ cycle number, the end cycle of the selected portion is $35^{th}$ cycle number in the second data set.

In one embodiment, the end cycle of the selected portion is any one of a cycle number corresponding to the axis of symmetry and fifteen (15) consecutive cycle numbers immediately before the cycle number corresponding to the axis of symmetry; any one of a cycle number corresponding to the axis of symmetry and ten (10) consecutive cycle numbers immediately before the cycle number corresponding to the axis of symmetry; any one of a cycle number corresponding to the axis of symmetry and seven (7) consecutive cycle numbers immediately before the cycle number corresponding to the axis of symmetry; any one of a cycle number corresponding to the axis of symmetry and six (6) consecutive cycle numbers immediately before the cycle number corresponding to the axis of symmetry; any one of a cycle number corresponding to the axis of symmetry and five (5) consecutive cycle numbers immediately before the cycle number corresponding to the axis of symmetry; any one of a cycle number corresponding to the axis of symmetry and four (4) consecutive cycle numbers immediately before the cycle number corresponding to the axis of symmetry; any one of a cycle number corresponding to the axis of symmetry and three (3) consecutive cycle numbers immediately before the cycle number corresponding to the axis of symmetry; any one of a cycle number corresponding to the axis of symmetry and two (2) consecutive cycle numbers immediately before the cycle number corresponding to the axis of symmetry; or any one of a cycle number corresponding to the axis of symmetry and a cycle number immediately before the cycle number corresponding to the axis of symmetry in the second data set.

In a particular embodiment, the end cycle of the selected portion is any one of a cycle number corresponding to the axis of symmetry and five consecutive cycle numbers immediately before the cycle number corresponding to the axis of symmetry in the second data set. For example, if the cycle number corresponding to the axis of symmetry in the slope data set is $35^{th}$ cycle number, the end cycle of the selected portion is $35^{th}$ cycle number, $34^{th}$ cycle number, $33^{rd}$ cycle number, $32^{nd}$ cycle number, $31^{st}$ cycle number, or $30^{th}$ cycle number in the second data set.

In one embodiment, the end cycle of the selected portion is a cycle number corresponding to the axis of symmetry in the second data set. For example, if the cycle number corresponding to the axis of symmetry in the slope data set is $35^{th}$ cycle number, the end cycle of the selected portion is $35^{th}$ cycle number in the second data set.

According to one embodiment, the selected portion of the second data set of step (c) is within a range from a first cycle number to a cycle number having a maximum slope value. In other word, each of the start cycle and the end cycle is selected within a range from a first cycle number to a cycle number having a maximum slope value.

As an example, the selected portion of the second data set of step (c) may range from a first cycle number to a cycle number having a maximum slope value. As another example, the selected portion of the second data set of step (c) may range from a second cycle number to a cycle number having a maximum slope value. As still another example, the selected portion of the second data set of step (c) may range from a third cycle number to a cycle number having a maximum slope value.

As a further example, the selected portion of the second data set of step (c) may range from a third cycle number to any one of three consecutive cycle numbers immediately before a cycle number having a maximum slope value in the second data set.

In an embodiment, the selected portion of the second data set of step (c) comprises, but not limited to, at least 5 cycles, at least 8 cycles, at least 10 cycles, at least 15 cycles, at least 20 cycles, or at least 30 cycles.

In an embodiment, the selected portion of the second data set is all or part of the slope data set.

In one embodiment, the selected portion of the second data set consists of consecutive cycles. In another embodiment, the selected portion of the second data set consists of nonconsecutive cycles. For example, the selected portion of the second data set may consist of odd numbered cycles, such as $3^{rd}$, $5^{th}$, $7^{th}$, $9^{th}$, $11^{th}$, $13^{th}$, and $15^{th}$ cycle numbers, or consist of even numbered cycles, such as $4^{th}$, $6^{th}$, $8^{th}$, $10^{th}$, $12^{th}$, $14^{th}$, and $16^{th}$ cycle numbers. In still another embodiment, the selected portion of the second data set consists of some consecutive cycles and some nonconsecutive cycles, such as $3^{rd}$-$6^{th}$, $10^{th}$, $12^{th}$, $14^{th}$-$18^{th}$ cycles.

The selected portion of the second data set may be selected directly by a user or automatically by a computer system, in consideration of the requirements as above.

The selected portion of the second data set may comprise additional data points that were not originally in the slope data set.

In an embodiment, the selected portion of the second data set further comprises one or more additional data points after the end cycle of the selected portion, the one or more additional data points having a slope value equal to the slope value at the end cycle number of the selected portion.

For positive samples containing a target analyte but now showing a typical S-shaped amplification curve, e.g., positive samples where no plateau region is observed in an amplification curve, the method of the present invention may often produce as a Ct value a first derivative maximum (FDM) larger than the end cycle number of the slope data set, resulting in false negative results. However, these false negative results can be avoided by inserting additional data points corresponding to the plateau region into the selected portion of the second data set.

The additional data points to be included or inserted in the selected portion of the second data set should have a slope value equal to the slope value at the end cycle number of the selected portion, and may be 1-40, 1-30, 1-20, or 1-10 data points, more particularly two, three, four, five, six, seven, eight, nine, or ten data points.

In an example, where the slope value at the end cycle number of the selected portion of the second data set is "800", the number of the additional data points to be included is 10, and the slope value of the additional data points is "800".

As used herein, a first value which is "equal to" a second value is intended to encompass not only the case where the first value is "exactly the same as" the second value, but also the case where the first value is "substantially the same as" the second value.

Then, an S-shaped function that approximates the selected portion is calculated.

The phrase "calculating an S-shaped function" as used herein means a process of producing a best-fit S-shaped function to the data points of the selected portion. The process of calculating the S-shaped function may be referred to herein as S-shaped regression analysis. The S-shaped function can be calculated using a fitting method known in the art.

According to one embodiment, calculating an S-shaped function in step (c) comprises fitting the data points of the selected portion to a conventional S-shaped function known in the art; and determining the best fit function and its parameters.

According to another embodiment, calculating an S-shaped function in step (c) comprises determining parameters of a specific S-shaped function. Specifically, calculating an S-shaped function in step (c) comprises fitting the data points of the selected portion to a specific S-shaped function; and determining parameters of the best fit S-shaped function.

The S-shaped function used in the methods of the present invention may be a function well known in the art to approximate a growth curve, particularly an amplification curve, and more particularly a real time PCR curve for a target analyte.

Examples of the S-shaped regression function may include, but are not limited to, a sigmoid function, a logistic function, a Gompertz function, and a Chapman function.

In an embodiment, the S-shaped function is represented by any one of Equations II-IV as detailed below.

(a) Sigmoid Function

Sigmoid function is a special case of the logistic function and also has a characteristic S-shaped curve or sigmoid curve, which may be represented by Equation II below:

$$f(x) = \alpha_1 + \frac{\alpha_2 - \alpha_1}{1 + 10^{\alpha_4(\alpha_3 - x)}} \qquad \text{Equation II}$$

wherein $\alpha_1$, $\alpha_2$, $\alpha_3$, and $\alpha_4$ are parameters as determined by fitting of the sigmoid function to the selected portion of the slope data set, and x is a cycle number.

In the equation, $\alpha_1$ may correspond to the background value in the curve represented by the function; $\alpha_2$ may correspond to the maximum value in the curve represented by the function; $\alpha_3$ may correspond to a cycle number with a median in the curve represented by the function; $\alpha_4$ may correspond to the slope of the curve represented by the function.

(b) Logistic Function

Logistic function is a function having a characteristic S-shaped curve or sigmoid curve, which may be represented by Equation III below:

$$f(x) = \alpha_1 + \frac{\alpha_2 - \alpha_1}{1 + (x/\alpha_3)^{\alpha_4}} \qquad \text{Equation III}$$

wherein $\alpha_1$, $\alpha_2$, $\alpha_3$, and $\alpha_4$ are parameters as determined by fitting of the logistic function to the selected portion of the slope data set, and x is a cycle number.

In the equation, $\alpha_1$ may correspond to the background value in the curve Da represented by the function; $\alpha_2$ may correspond to the maximum value in the curve represented by the function; $\alpha_3$ may correspond to a cycle number with a median in the curve represented by the function; $\alpha_4$ may correspond to the slope of the curve represented by the function.

(c) Gompertz Function

Gompertz function is a kind of sigmoid function, and has a curve in the form of ascending steeply and gradually approaching to a horizontal line, which may be represented by Equation IV below:

$$f(x) = \alpha_1 + (\alpha_2 - \alpha_1)10^{-e^{(\alpha_3 - x)/\alpha_4}} \qquad \text{Equation IV}$$

wherein $\alpha_1$, $\alpha_2$, $\alpha_3$, and $\alpha_4$ are parameters as determined by fitting of the Gompertz function to the selected portion of the slope data set, and x is a cycle number.

In the equation, $\alpha_1$ may correspond to the background value in the curve represented by the function; $\alpha_2$ may correspond to the maximum value in the curve represented by the function; $\alpha_3$ may correspond to a cycle number with a median in the curve represented by the function; $\alpha_4$ may correspond to the slope of the curve represented by the function.

(d) Chapman Function

Chapman function is a kind of sigmoid function, which may be represented by Equation V below:

$$f(x) = \alpha_1 + (\alpha_2 - \alpha_1)(1 - 10^{-\alpha_4 x})^c \qquad \text{Equation V}$$

wherein $\alpha_1$, $\alpha_2$, $\alpha_3$, and $\alpha_4$ are parameters as determined by fitting of the Chapman function to the selected portion of the slope data set, and x is a cycle number.

In the equation, $\alpha_1$ may correspond to the background value in the curve represented by the function; $\alpha_2$ may correspond to the maximum value in the curve represented by the function; c is an additional parameter; $\alpha_4$ may correspond to the slope of the curve represented by the function.

For further description on the S-shaped function, see Michele Guescini et al., BMC Bioinformatics 2008, 9:326.

According to one embodiment, a computer system is used to calculate a function that fits to the data points of the selected portion. The computer system includes a computer readable storage medium having stored thereon a computer program capable of performing a regression analysis and a processor capable of executing the computer program.

As described above, the S-shaped function may be a predetermined function, and the regression analysis may be a process of determining parameters of the S-shaped function.

Specifically, when the cycle at a data point is set as the independent variable x and the signal value at the cycle is set as the dependent variable y, the dependent variable is represented by a polynomial function of the independent variable.

Step (d): Using S-Shaped Function to Detect Target Analyte

Then, the resulting S-shaped function is used to detect the target analyte in a sample.

The term "detect", "detecting" or "detection" as used herein is intended to encompass both "qualification" and "quantification (quantitation)" of a target analyte. The term "qualification" or "qualitative analysis" as used herein refers to determining the presence of a target analyte in a sample using an S-shaped function; while the term "quantification" or "quantitative analysis" as used herein refers to determining the initial amount of a target analyte in a sample using an S-shaped function.

As used herein, the phrase "using the S-shaped function" is used to encompass using the S-shaped function, either directly or indirectly. For example, using the S-shaped function directly involves detecting a target analyte by using the parameter values of the S-shaped function, while using the S-shaped function indirectly involves detecting a target analyte by using the shape of an S-shaped function.

In one embodiment, using the S-shaped function in step (d) comprises determining a threshold cycle (Ct) value from the S-shaped function. The Ct value is used for the qualification or quantitation of a target analyte in a sample.

Determining a Ct value from an S-shaped function may be performed by various methods as follows:

a. Determination of a Ct Value by Use of a Threshold;

In one embodiment, determining a Ct value from an S-shaped function comprises applying a threshold to an S-shaped curve represented by the function. In general, the intersection between the S-shaped curve and the threshold can be determined as a Ct value.

The threshold applied to the S-shaped curve may be determined by a conventional method known in the art. The threshold applied to the S-shaped curve may be determined in consideration of background slope values, sensitivity, characteristics of labels, or signal variations from detector to detector. The threshold applied to the S-shaped curve may be determined such that it has the same value as any slope value in an exponential region of the S-shaped curve. The threshold applied to the S-shaped curve may be determined such that it is higher than the slope values in the baseline region but less than the slope values in the plateau region of the S-shaped curve. Alternatively, the threshold applied to the S-shaped curve may be determined such that it has a value obtained by multiplying a standard deviation of slope values in the baseline region of the S-shaped curve by a constant value (e.g., 10).

The threshold may be determined either directly by the operator or automatically by the detector. The threshold may be empirically determined through repeated experiments on the target analyte. Alternatively, the threshold may be determined by a mathematical calculation.

b. Determination of a Ct Value by Use of an $n^{th}$ Derivative Maximum of the Function In one embodiment, determining a Ct value from an S-shaped function comprises (i) calculating a first, second, or $n^{th}$ order derivative of the S-shaped function, wherein n is a natural number; and (ii) determining a cycle number having a maximum of the first, second or $n^{th}$ derivative as a Ct value.

In a particular embodiment, the Ct value is a cycle number having a maximum of the first derivative of the S-shaped function.

c. Determination of a Ct Value by Use of Parameters of the Function

In one embodiment, using an S-shaped function in step (d) comprises determining a Ct value from the parameters of the S-shaped function.

Determining a Ct value from the parameters of the S-shaped function may comprise determining as a Ct value the value of a specific parameter, determining as a Ct value the value calculated by a formula including a specific parameter, or determining as a Ct value the value calculated by a formula including a plurality of parameters.

For example, where the S-shaped function represented by Equation II is used, the cycle number having a first derivative maximum of the function corresponds to the value of the parameter $\alpha_3$. Thus, using an S-shaped function in step (d) comprises determining the value of the parameter $\alpha_3$ as a Ct value.

It is to be understood by those skilled in the art that in addition to the methods described above, other methods known in the art may be used to determine Ct values.

The threshold cycle as determined by the method described above can be used for qualitative or quantitative analysis of a target analyte in a sample, as follows:

a. Qualitative Analysis

In qualitative analysis, a sample which does not have a Ct value determined or a sample which has a Ct value determined, but greater than the end cycle number in the data set of step (a) or (b) is determined to contain no target analyte (i.e., a negative sample), whereas a sample having a Ct value determined less than or equal to the end cycle number in the data set of step (a) or (b) is determined to contain the target analyte (i.e., a positive sample).

For example, if the Ct value obtained from an unknown sample by the method of the present invention is 35 and the end cycle in the data set of step (a) or step (b) is 50, then the sample is determined to be a positive; whereas if the Ct value is 70 and the end cycle in the data set of step (a) or step (b) is 50, then the sample is determined to be a negative.

b. Quantitative Analysis

In quantitative analysis, serial dilutions of a standard target analyte are subjected to an amplification reaction, respectively, to obtain a plurality of amplification curves, and then Ct values are determined from the amplification curves by the method of the invention described above. Thereafter, the Ct values are plotted against log transformed concentrations of the standard target analytes to obtain a standard curve for quantification. Then, an unknown sample (whose initial amount is unknown) is subjected to an amplification reaction to obtain a Ct value, which is then applied to the standard curve to determine the initial amount of unknown sample.

Qualitative or quantitative analysis using such a Ct value can be performed according to various methods known in the art.

II. Detection of Target Analyte Using Slope Data Set (Including Filtering-Out Step)

In another aspect of the invention, the method of the invention may further comprise filtering out a first data set.

Specifically, the method of the present invention may further comprise the following steps, between steps (a)-(b):

(a1) applying a threshold value to the first data set; and (a2) proceeding to the next step (b), if the first data set has a signal value exceeding the threshold value.

Typically, in the case of negative samples that do not contain a target analyte, the first data set obtained in step (a) as well as the second data set obtained in step (b) will have significantly low signal values over all cycle numbers, and in particular the second data set from the negative sample will not exhibit a pattern like an amplification curve or a growth curve, that is, the slope value does not increase as the cycle number increases. This can make it difficult to obtain an S-shaped function that approximates a selected section of the second data set. Therefore, it would be desirable to ensure that the method of the present invention is not applied to negative samples.

In this respect, the method of the invention comprises filtering out a data set, i.e., removing a data set, that is expected to be from a negative sample and obtaining only a data set that is expected to be from a positive sample.

In step (a1), a threshold value is applied to the first data set of step (a) to distinguish between the data set from a positive sample and the data set from a negative sample. This distinction may be easily achieved by applying a threshold. After applying a threshold to the first data set of step (a), it is determined that the data set with a signal value above the threshold value is from a positive sample, and the data set with signal values all below the threshold is from a negative sample.

Then, in step (a2), the next step (b) proceeds, if the first data set has a signal value exceeding the threshold value. A data set with a signal value exceeding the threshold value is expected to be from a positive sample, and thus generate a best fit S-shaped function according to the method of the present invention.

On the other hand, if the first data set has signal values all below the threshold value, then step (b) does not proceed. A data set with signal values all below the threshold value is expected to be from a negative sample, and therefore may not be able to generate a best fit S-shaped function according to the method of the present invention. The data set with signal values all below the threshold value can indicate the absence of a target analyte even without proceeding to step (b).

III. Detection of Target Analyte Using Slope Data Set (Including Filtering-Out Step)

In still another aspect of the invention, the method of the invention may further comprise filtering out a second data set.

Specifically, the method of the present invention may further comprise the following steps, between steps (b)-(c):

(b1) applying a threshold value to the second data set; and (b2) proceeding to the next step (c), if the second data set has a slope value exceeding the threshold value.

Since the method of section III above is the same as that of section II except that the threshold value is applied to the second data set, not to the first data set, the common descriptions between them are omitted in order to avoid undue redundancy leading to the complexity of this specification.

However, it is noted that the threshold value applied to the method of section III may be different from the threshold applied to the method of section II.

IV. Storage Medium, Device, and Computer Program

In further aspect of this invention, there is provided a computer readable storage medium containing instructions to configure a processor to perform a method for detecting a target analyte in a sample, the method comprising:

(a) receiving a first data set representing a growth curve by an amplification reaction for a target analyte; wherein said first data set includes a plurality of data points, each having a cycle number and a signal value at the cycle number;

(b) calculating a slope value at each cycle number for the first data set to obtain a second data set; wherein said second data set includes a plurality of data points, each having a cycle number and a slope value at the cycle number;

(c) calculating an S-shaped function that approximates a selected portion of the second data set; and (d) using the S-shaped function to detect the target analyte in a sample.

In further aspect of this invention, there is provided a computer program to be stored in a computer readable storage medium to configure a processor to perform a method for detecting a target analyte in a sample, the method comprising:

(a) receiving a first data set representing a growth curve by an amplification reaction for a target analyte; wherein said first data set includes a plurality of data points, each having a cycle number and a signal value at the cycle number;

(b) calculating a slope value at each cycle number for the first data set to obtain a second data set; wherein said second data set includes a plurality of data points, each having a cycle number and a slope value at the cycle number;

(c) calculating an S-shaped function that approximates a selected portion of the second data set; and (d) using the S-shaped function to detect the target analyte in a sample.

Since the storage medium, the device and the computer program of the present invention described hereinbelow are intended to perform the present methods in a computer, the common descriptions between them are omitted in order to avoid undue redundancy leading to the complexity of this specification.

The program instructions are operative, when performed by the processor, to cause the processor to perform the present method described above. The program instructions for performing the present method may comprise (i) an instruction to receive a first data set representing a growth curve by a signal amplification reaction for a target analyte; (ii) an instruction to calculate a slope value at each cycle number for the first data set to obtain a second data set; (iii) an instruction to calculate an S-shaped function that approximates a selected portion of the second data set; and (iv) an instruction to detect the target analyte in a sample using the S-shaped function.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The first data set may be received through several mechanisms. For example, the first data set may be acquired by a processor resident in a PCR data acquiring device. The first data set may be provided to the processor in real time or may be stored in a memory unit or buffer and provided to the processor after the experiment has been completed. Similarly, the first data set may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In a further aspect of this invention, there is provided a device for detecting a target analyte in a sample, comprising (a) a computer processor, and (b) the computer readable storage medium described above coupled to the computer processor.

According to an embodiment, the device further comprises a reaction vessel to accommodate the sample and signal-generating means, a temperature controlling means to control temperatures of the reaction vessel and/or a detector to detect signals at cycles.

The processor may be prepared in such a manner that a single processor can do several performances. Alternatively, the processor unit may be prepared in such a manner that several processors do the several performances, respectively.

According to an embodiment, the processor may be embodied by installing software into conventional devices for detection of target nucleic acid sequences (e.g. real-time PCR device).

The features and advantages of this invention will be summarized as follows:

(a) The present invention provides a novel method for detecting a target analyte in a sample using an S-shaped function that approximates a selected portion of the slope data set.

(b) The present invention provides a method for obtaining a threshold cycle (Ct) value from the parameters of an S-shaped function that approximates a selected portion of the slope data set even without using a threshold.

(c) The method of the present invention allows for more accurate detection of target analytes without being affected by signal variations between reactions or apparatuses.

(d) Conventional methods for detecting a target analyte by using a best-fit S-shaped function to a raw data set require a complicated baseline slope correction in order to increase the goodness of fit of the function, while the method of the present invention can rule out such baseline slope correction.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Detection of Target Analyte Using S-Shaped Function for Slope Data Set (Embodiment 1)

It was examined whether a target analyte could be detected using an S-shaped function for a slope data set, according to an embodiment of the present invention.

Detection of the target analyte was carried out as follows: (i) obtaining a raw data set (i.e., first data set herein) for a target analyte, (ii) obtaining a slope data set (i.e., second data set herein) by calculating a slope value at each cycle number (and optionally filtering out the slope data set), (iii) obtaining an S-shaped function that approximates a selected portion of the slope data set, and (iv) using the S-shaped function to detect the target analyte.

<1-1> Performing Real-Time Polymerase Chain Reaction and Obtaining Raw Data Set

A genomic DNA of *Neisseria gonorrhoeae* (NG) (Koram Deo Lab., Korea; ATCC 700825) was used as a target analyte. In order to amplify the target analyte and generate a signal from its amplification product, a real-time PCR was performed in the presence of a pair of primers and a TaqMan probe as described in Table 1 below.

TABLE 1

BHQ: Quencher (Black Hole Quencher)

| Name | Type | Sequence (5' → 3') | SEQ ID NO |
|---|---|---|---|
| NG_F | Forward primer | TACGCCTGCTACTTTCACGCT | 1 |
| NG_R | Reverse primer | CAATGGATCGGTATCACTCGC | 2 |
| NG_P | Probe | [FAM]TGCCCCTCA1TGGCGT GTTTCG[BHQ-1] | 3 |

The real time PCR was performed in the final volume of 20 μl containing 10 pmole of forward primer (SEQ ID NO: 1), 10 pmole of reverse primer (SEQ ID NO: 2), 5 pmole of TaqMan probe (SEQ ID NO: 3), either a target analyte (100 pg, 10 pg, 1 pg, or 100 fg of NG genomic DNA) or sterile distilled water as a negative control (NTC), and 10 μl of 2× Master Mix (final, 200 μM dNTPs, 2.5 mM $MgCl_2$, 1.6 U Taq DNA polymerase) (Solgent, Korea). The tubes containing the reaction mixture were placed on the real-time thermocycler (CFX96 Real-time Cycler, Bio-Rad) for 15 min at 95° C., followed by 50 cycles of 30 sec at 95° C., 60 sec at 60° C., and 30 sec at 72° C. Detection of fluorescence was performed at 60° C. at each cycle.

Figure 2:
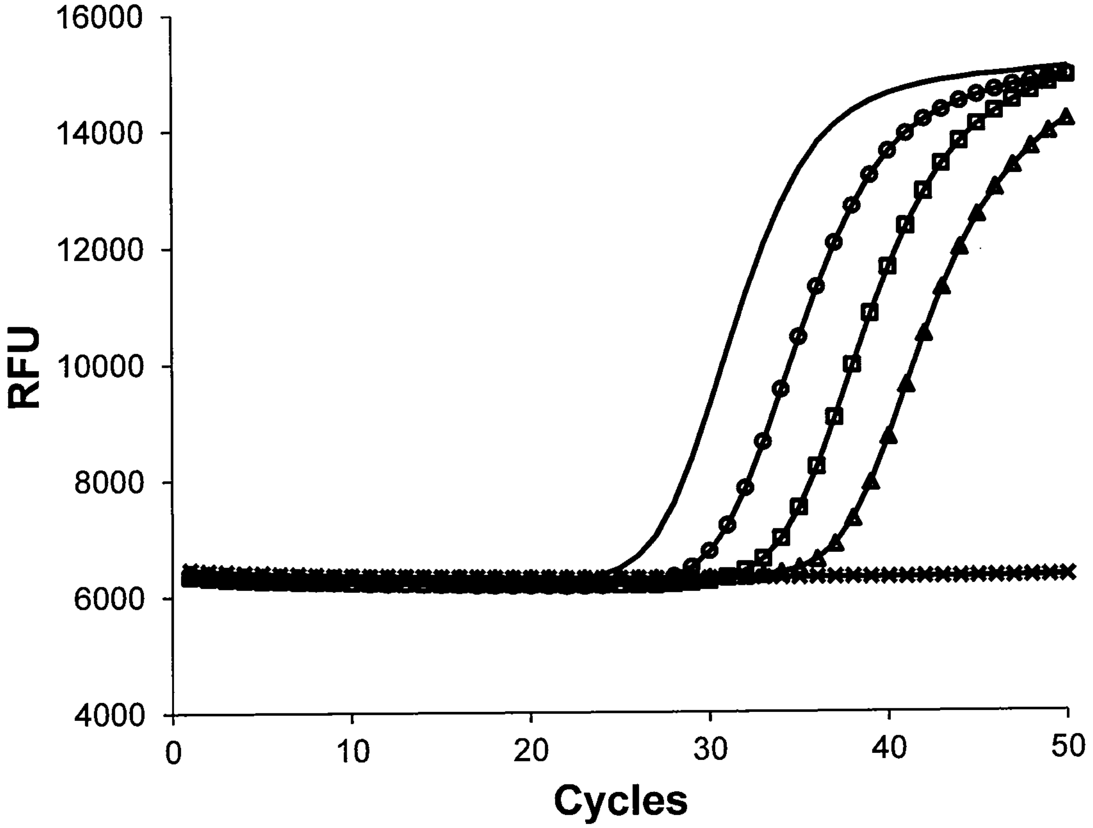
FIG. 2 shows five raw data sets obtained by amplification reactions using samples containing a genomic DNA of *Neisseria gonorrhoeae* (NG) at various concentrations (100 pg, 10 pg, 1 pg, and 100 fg) as a target analyte and a sample not containing the target analyte (NTC), in accordance with the method of Example 1 (solid line, NG 100 pg; -○-, NG 10 pg; -□-, NG 1 pg; and -Δ-, NG 100 fg; -X-, NTC).

As a result, five raw data sets, i.e., data sets not baseline-subtracted, were obtained from the samples containing varying concentrations of the target analytes. The results are depicted in FIG. 2 (solid line, NG 100 pg; -○-, NG 10 pg; -□-, NG 1 pg; and -Δ-, NG 100 fg; -X-, NTC).

<1-2> Obtaining Slope Data Set

A slope value at each cycle number was calculated by using a signal value at each cycle number in the raw data set of Example <1-1>, to obtain a slope data set.

Specifically, calculation of the slope values using the signal values was performed by the difference method as shown in Equation VI below.

$$\Delta y_i = y_i - y_{i-1} \qquad \text{Equation VI}$$

wherein i is a cycle number in a raw data set; $y_i$ is a signal value at $i^{th}$ cycle number; and $\Delta y_i$ is a slope value at $i^{th}$ cycle number, with a proviso that when i is 0, $\Delta y_1=0$.

Figure 3:
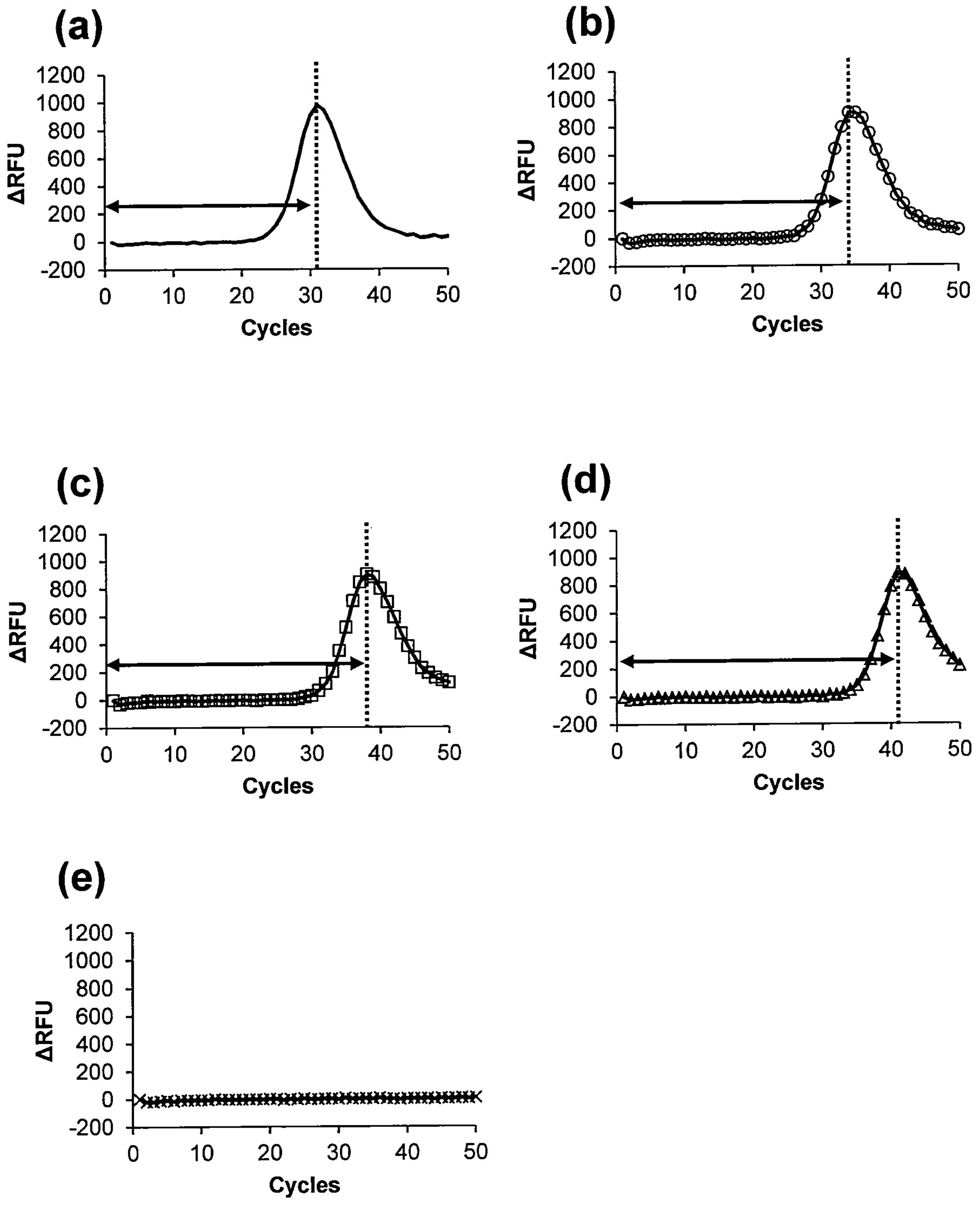
FIG. 3 shows five slope data sets for samples containing a genomic DNA of *Neisseria gonorrhoeae* (NG) at various concentrations as a target analyte and for a sample not containing the target analyte (NTC) in accordance with the method of Example 1 ((a): NG 100 pg; (b): NG 10 pg; (c): NG 1 pg; (d): NG 100 fg; and (e): NTC). The double arrow in each of the slope data sets indicates a selected portion for obtaining an S-shaped function.

The resulting five slope data sets for samples containing various concentrations of the target analytes and for a sample not containing the target analyte are shown in FIG. 3 ((a): NG 100 pg; (b): NG 10 pg; (c): NG 1 pg; (d): NG 100 fg; and (e): NTC).

<1-3> Filtering Out Slope Data Set (Optional)

Among the five slope data sets obtained in Example <1-2>, a slope data set having no significant slope value was filtered out.

For filtering out, a filtering threshold value 100 (unit: ΔRFU) was applied to each of the slope data sets. After applying the threshold value, a slope data set having a slope value equal to or greater than the filtering threshold continued to the next step, while the data set having all slope values less than the filtering threshold was determined to be negative without proceeding to the next step.

As a result, four slope data sets for the samples containing various concentrations of the target analytes (see graphs (a)-(d) in FIG. 3) were found to have a slope value above the filtering threshold. In contrast, only a slope data set for the sample not containing the target analyte (see graph (e) in FIG. 3) was found to have slope values all below the filtering threshold, and was filtered out as a negative sample.

<1-4> Calculating S-Shaped Function for Selected Portion of Slope Data Set

For calculation of an S-shaped function, a portion was selected from each of the slope data sets in Example <1-3>. The selected portion for each of the slope data sets ranged from the first cycle number to the cycle number having a maximum slope value.

The selected portion for each of the slope data sets was from $1^{st}$ to $31^{st}$ cycle numbers (see graph (a) in FIG. 3), from $1^{st}$ to $34^{th}$ cycle number (see graph (b) in FIG. 3), from $1^{st}$ to $38^{th}$ cycle numbers (see graph (c) in FIG. 3), and from $1^{st}$ to $41^{st}$ cycle numbers (see graph (d) in FIG. 3), respectively. The selected portion is indicated by a double arrow in each slope data set of FIG. 3.

Then, an S-shaped function that approximates each of the selected portions was calculated. In this Example, the sigmoid function represented by Equation II below was used as an example of the S-shaped function.

$$f(x) = \alpha_1 + \frac{\alpha_2 - \alpha_1}{1 + 10^{\alpha_4(\alpha_3 - x)}} \quad \text{Equation II}$$

wherein $\alpha_1$, $\alpha_2$, $\alpha_3$, and $\alpha_4$ are parameters as determined by fitting of the sigmoid function to the selected portion of the slope data set, and x is a cycle number.

Fitting of the sigmoid function to the selected portion of the slope data set was performed according to a conventional LM algorithm (Levenberg-Marquardt algorithm; see Christian Kanzow et al., JCAM, 172 (2): 375 (2004)), thereby obtaining the sigmoid function that approximates the selected portion of the slope data set.

Figure 4:
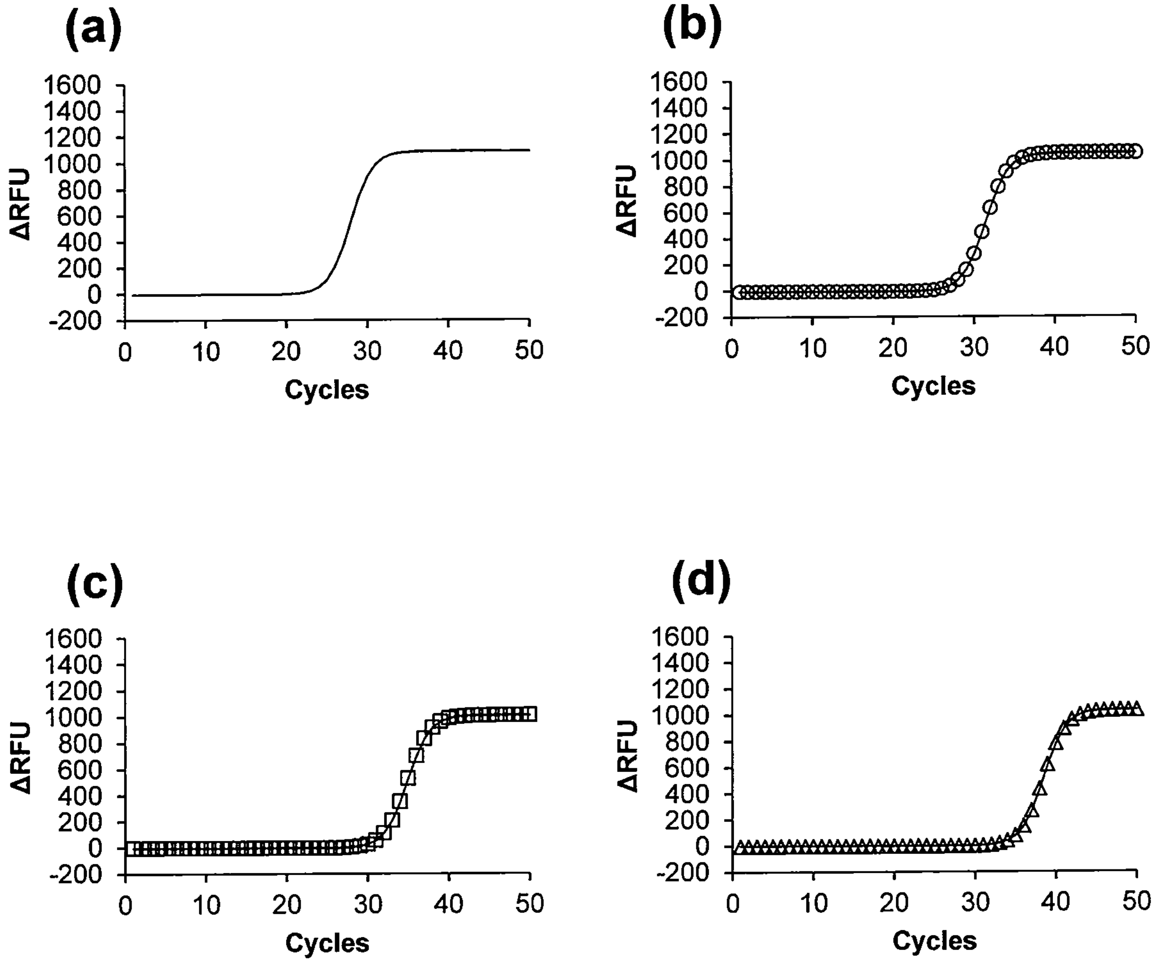
FIG. 4 shows four curves produced by the sigmoid function that approximates each of the selected portions of the slope data sets for samples containing genomic DNA of *Neisseria gonorrhoeae* (NG) at various concentrations as a target analyte in accordance with the method of Example 1 ((a): NG 100 pg; (b): NG 10 pg; (c): NG 1 pg; (d): NG 100 fg).

The resulting four sigmoid functions (in the form of a sigmoid curve) for the samples containing various concentrations of genomic DNAs of *Neisseria gonorrhoeae* (NG) as target analytes are depicted in FIG. 4 ((a): NG 100 pg; (b): NG 10 pg; (c): NG 1 pg; and (d): NG 100 fg). In addition, the values of the parameters for each sigmoid function are shown in Table 2 below.

TABLE 2

| | Parameter value | | | |
|---|---|---|---|---|
| Parameter | 100 pg | 10 pg | 1 pg | 100 fg |
| $\alpha_1$ | −5 | −8 | −5 | −3 |
| $\alpha_2$ | 1092 | 1051 | 1008 | 1035 |
| $\alpha_3$ | 27.92 | 31.40 | 34.85 | 38.44 |
| $\alpha_4$ | 0.322 | 0.307 | 0.312 | 0.313 |

<1-5> Detection of Target Analyte Using Threshold

A detection threshold value was applied to each of the four sigmoid curves obtained in Example <1-4> to determine the intersection between each of the curves and the threshold value as a threshold cycle (Ct). The detection threshold value was 100 (unit: ΔRFU), which corresponds to approximately 10% of the parameter value $\alpha_2$ for the sigmoid functions.

Thereafter, a sample having a slope value above the detection threshold value, i.e., a sample having a Ct value, was determined to be positive, while a sample having all slope values below the detection threshold value, i.e., a sample having no Ct value, was determined to be negative.

The results are shown in Table 3 below.

TABLE 3

| | Target analyte | | | | |
|---|---|---|---|---|---|
| | Positive | | | | Negative |
| Concentration | 100 pg | 10 pg | 1 pg | 100 fg | — |
| Filtering threshold | | | 100 | | |
| Maximum slope value | 978 | 901 | 901 | 888 | 8 |
| Proceed to next step | Yes | Yes | Yes | Yes | No |
| Detection threshold | | | 100 | | |
| Ct value | 24.87 | 28.27 | 31.81 | 35.31 | — |
| Result | Positive | Positive | Positive | Positive | Negative |

As shown in Table 3, the samples containing varying concentrations of target analytes were found to have Ct values of 24.87, 28.27, 31.81, and 35.31, respectively, and thus were all determined to be positive.

Example 2: Detection of Target Analyte Using S-Shaped Function for Slope Data Set (Embodiment 2)

As an alternative approach for obtaining Ct values, a cycle number having a first derivative maximum (FDM) of the sigmoid function was used as a Ct value.

The FDM cycle number of the sigmoid function was determined by calculating the x value at which the second derivative of the sigmoid function equals to zero or by taking the parameter $\alpha_3$ of the sigmoid function. In particular, using the parameter $\alpha_3$ as the FDM cycle number eliminated the need to differentiate the sigmoid function.

Then, a sample whose FDM cycle number ($\alpha_3$) is less than or equal to the end cycle number of the slope data set, e.g., 50, was determined to be positive, while a sample whose FDM cycle number is greater than the end cycle number in the slope data set was determined to be negative.

The results are shown in Table 4 below.

TABLE 4

| | Target analyte | | | | |
|---|---|---|---|---|---|
| | Positive | | | | Negative |
| Concentration | 100 pg | 10 pg | 1 pg | 100 fg | — |
| Filtering threshold | | | 100 | | |
| Maximum slope value | 978 | 901 | 901 | 888 | 8 |
| Proceed to next step | Yes | Yes | Yes | Yes | No |
| FDM cycle number | 27.92 | 31.40 | 34.85 | 38.44 | — |
| Result | Positive | Positive | Positive | Positive | Negative |

As shown in Table 4, the samples containing various concentrations of target analytes were found to have the FDM cycle number ($\alpha_3$) of 27.92, 31.40, 34.85, and 38.44, respectively, and were all determined to be positive as the FDM cycle numbers were all less than 50.

Example 3: Detection of Target Analyte Using S-Shaped Function for Slope Data Set (Embodiment 3)

The procedure of Example 2 was repeated except for using logistic function, Gompertz function, and Chapman function, respectively, in place of the sigmoid function, thereby obtaining each S-shaped function that approximates a selected portion of the slope data set. Then, a cycle number having the first derivative maximum (FDM) was determined as a Ct value, which was used to detect the target analyte.

The logistic function used in this Example may be represented by Equation III below.

$$f(x) = \alpha_1 + \frac{\alpha_2 - \alpha_1}{1 + (x/\alpha_3)^{\alpha_4}} \quad \text{Equation III}$$

wherein $\alpha_1$, $\alpha_2$, $\alpha_3$, and $\alpha_4$ are parameters as determined by fitting of the logistic function to the selected portion of the slope data set, and x is a cycle number.

The Gompertz function used in this Example may be represented by Equation IV below.

$$f(x) = \alpha_1 + (\alpha_2 - \alpha_1)10^{-e^{(\alpha_3 - x)/\alpha_4}} \quad \text{Equation IV}$$

wherein $\alpha_1$, $\alpha_2$, $\alpha_3$, and $\alpha_4$ are parameters as determined by fitting of the Gompertz function to the selected portion of the slope data set, and x is a cycle number.

The Chapman function used in this Example may be represented by Equation V below.

$$f(x) = \alpha_1 + (\alpha_2 - \alpha_1)(1 - 10^{-\alpha_4 x})^c \quad \text{Equation V}$$

wherein $\alpha_1$, $\alpha_2$, $\alpha_3$, and $\alpha_4$ are parameters as determined by fitting of the Chapman function to the selected portion of the slope data set, and x is a cycle number.

Figure 5:
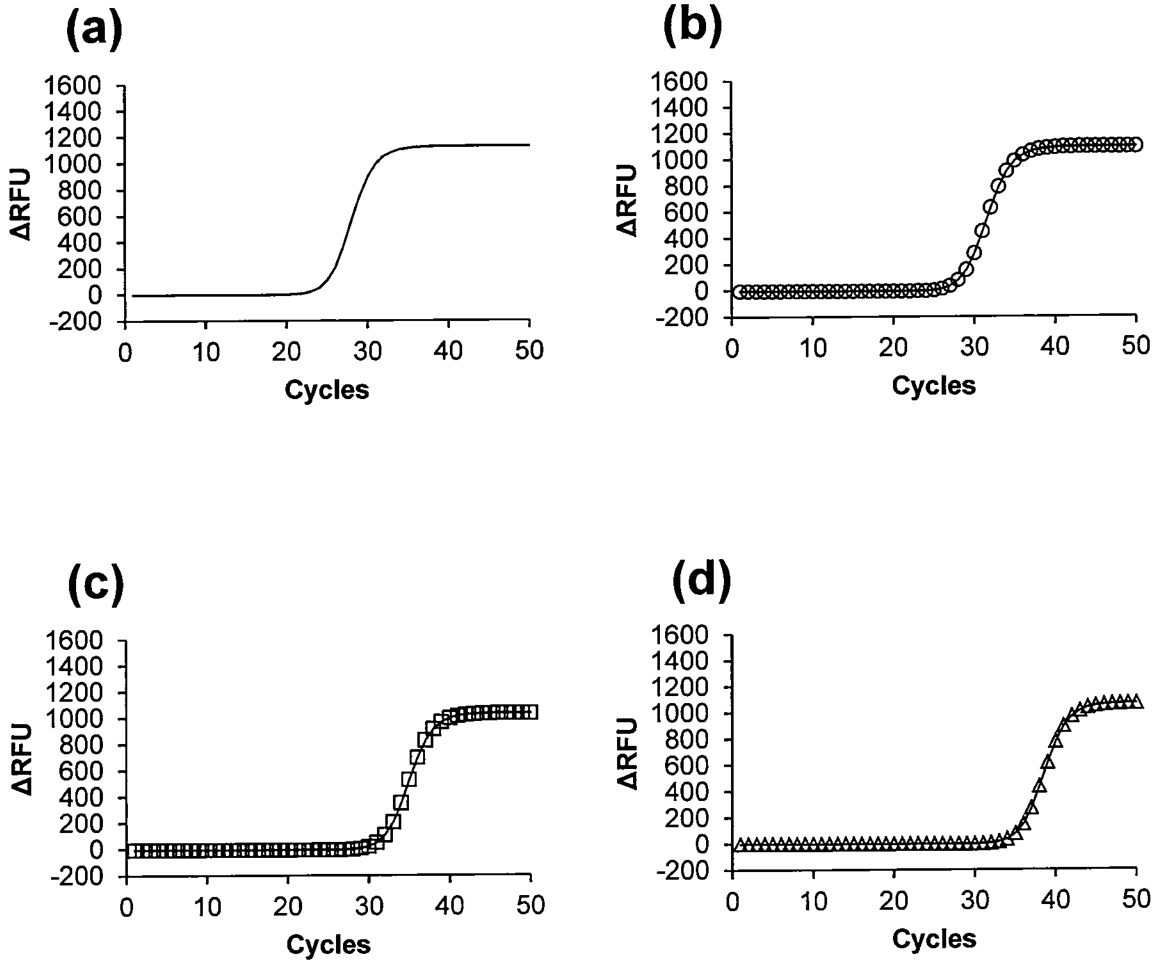
FIG. 5 shows four curves produced by the logistic function that approximates each of the selected portions of the slope data sets for samples containing genomic DNA of *Neisseria gonorrhoeae* (NG) at various concentrations as a target analyte in accordance with the method of Example 1 ((a): NG 100 pg; (b): NG 10 pg; (c): NG 1 pg; (d): NG 100 fg).
Figure 6:
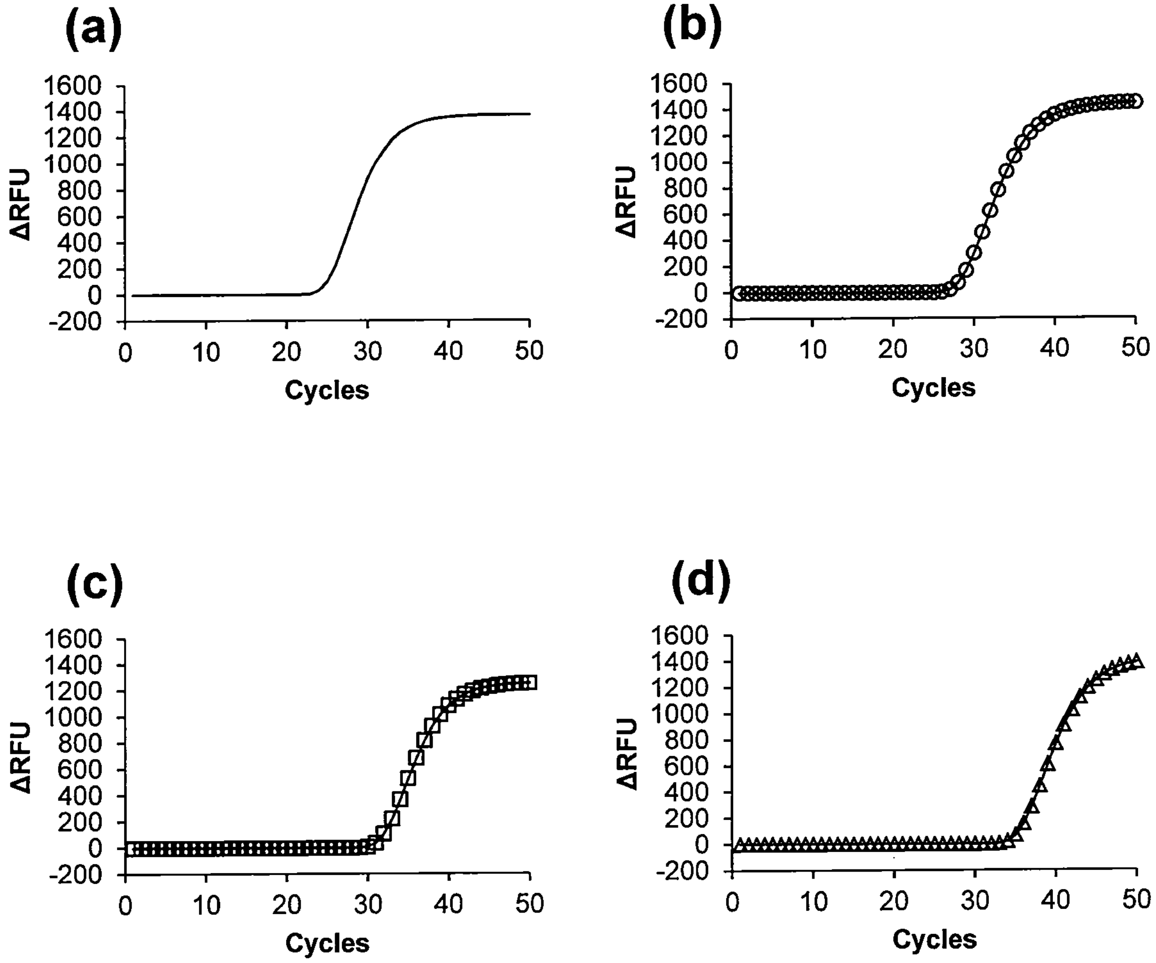
FIG. 6 shows four curves produced by the Gompertz function that approximates each of the selected portions of the slope data sets for samples containing genomic DNA of *Neisseria gonorrhoeae* (NG) at various concentrations as a target analyte in accordance with the method of Example 1 ((a): NG 100 pg; (b): NG 10 pg; (c): NG 1 pg; (d): NG 100 fg).
Figure 7:
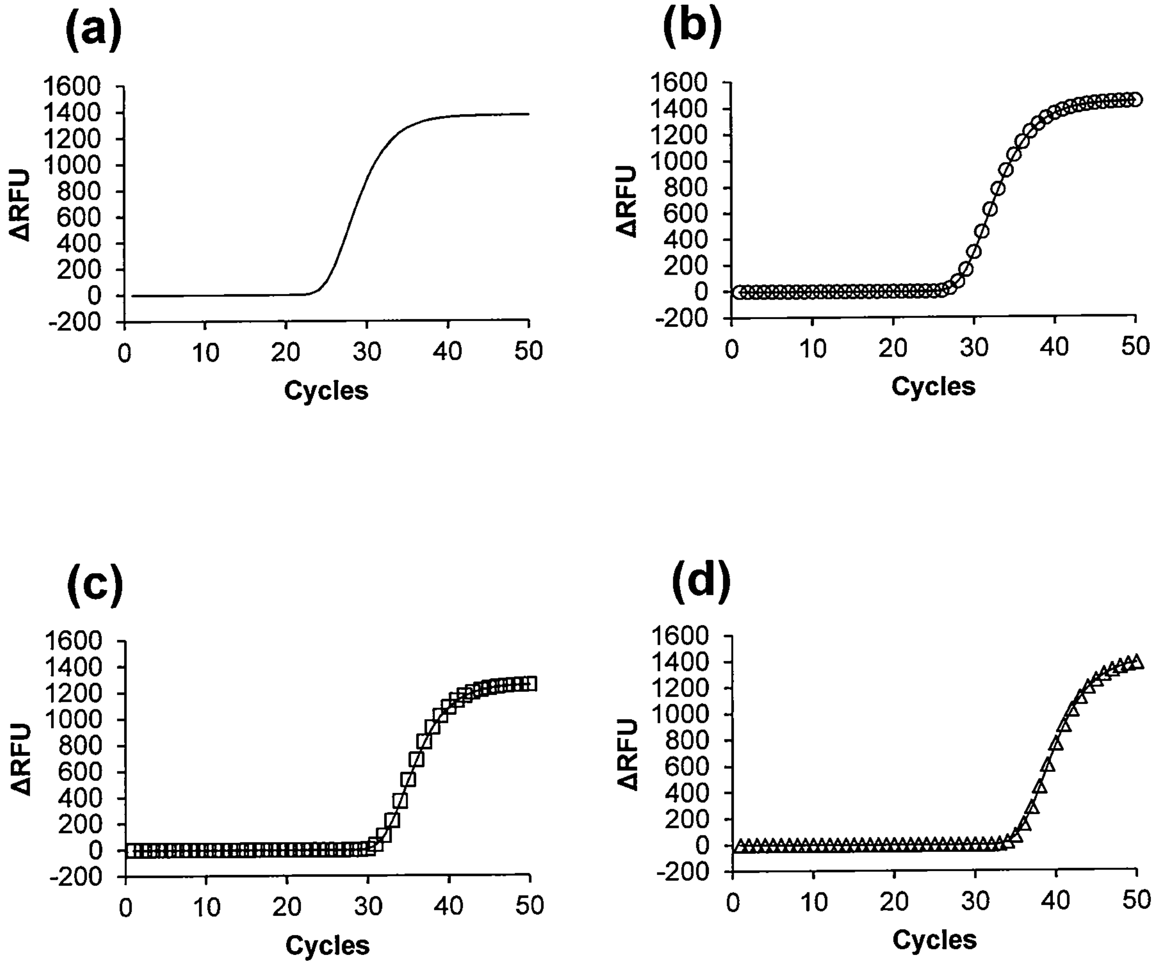
FIG. 7 shows four curves produced by the Chapman function that approximates each of the selected portions of the slope data sets for samples containing genomic DNA of *Neisseria gonorrhoeae* (NG) at various concentrations as a target analyte in accordance with the method of Example 1 ((a): NG 100 pg; (b): NG 10 pg; (c): NG 1 pg; (d): NG 100 fg).

The resulting curves representing logistic function, Gompertz function or Chapman function for various concentrations of target analytes are shown in FIGS. 5, 6 and 7, respectively ((a): NG 100 pg; (b): NG 10 pg; (c): NG 1 pg; and (d): NG 100 fg).

The parameter values for the logistic function, the Gompertz function, and the Chapman function are shown in Tables 5, 6 and 7, respectively.

TABLE 5

| | Logistic function | | | |
|---|---|---|---|---|
| parameter | NG 100 pg | NG 10 pg | NG 1 pg | NG 100 fg |
| $\alpha_1$ | −4 | −7 | −5 | −3 |
| $\alpha_2$ | 1134 | 1102 | 1041 | 1071 |
| $\alpha_3$ | 28.01 | 31.52 | 34.92 | 38.53 |
| $\alpha_4$ | −19.644 | −20.967 | −23.970 | −26.452 |

TABLE 6

| | Gompertz function | | | |
|---|---|---|---|---|
| parameter | NG 100 pg | NG 10 pg | NG 1 pg | NG 100 fg |
| $\alpha_1$ | −2 | −6 | −3 | −1 |
| $\alpha_2$ | 1369 | 1450 | 1261 | 1419 |
| $\alpha_3$ | 25.34 | 28.80 | 32.19 | 35.87 |
| $\alpha_4$ | 2.806 | 3.202 | 2.877 | 3.132 |

TABLE 7

| | Chapman function | | | |
|---|---|---|---|---|
| parameter | NG 100 pg | NG 10 pg | NG 1 pg | NG 100 fg |
| $\alpha_1$ | −2 | −6 | −3 | −1 |
| $\alpha_2$ | 1369 | 1450 | 1261 | 1419 |
| $\alpha_3$ | 19232.30 | 18534.91 | 166252.14 | 218144.76 |
| $\alpha_4$ | 0.155 | 0.136 | 0.151 | 0.139 |

The FDM cycle number of each function was determined by calculating the x value at which the second derivative of the function is zero.

The FDM cycle number of the logistic function can be calculated by Equation VII below.

$$FDM = \alpha_3 \sqrt[\alpha_4]{\frac{(\alpha_4 - 1)}{(\alpha_4 + 1)}} \quad \text{Equation VII}$$

The FDM cycle number of the Gompertz function can be calculated by Equation VIII below.

$$FDM = \ln(\ln(10))\alpha_4 + \alpha_3 \quad \text{Equation VIII}$$

The FDM cycle number of the Chapman function can be calculated by Equation IX below.

$$FDM = \frac{\ln(c)}{\ln(10)\alpha_4} \quad \text{Equation IX}$$

A sample whose FDM cycle number is equal to or less than the end cycle number, e.g., 50, was determined to be positive, while a sample whose FDM cycle number equal to or less than the end cycle number was determined to be negative.

The results are shown in Table 8 below.

TABLE 8

| S-shaped regression function | Concentration | Target analyte: Positive 100 pg | Positive 10 pg | Positive 1 pg | Positive 100 fg | Negative — |
|---|---|---|---|---|---|---|
| Logistic function | FDM cycle number | 28.02 | 31.53 | 34.92 | 38.53 | — |
| | Result | Positive | Positive | Positive | Positive | Negative |
| Gompertz function | FDM cycle number | 28.32 | 31.70 | 35.25 | 38.74 | — |
| | Result | Positive | Positive | Positive | Positive | Negative |

TABLE 8-continued

| S-shaped regression function | Concen-tration | Target analyte | | | | |
|---|---|---|---|---|---|---|
| | | Positive | | | | Negative |
| | | 100 pg | 10 pg | 1 pg | 100 fg | — |
| Chapman function | FDM cycle number | 27.68 | 31.47 | 34.58 | 38.48 | — |
| | Result | Positive | Positive | Positive | Positive | Negative |

As shown in Table 8, the FDM cycle numbers for the samples containing varying concentrations of target analytes (NG 100 pg, 10 pg, 1 pg and 100 fg) were all found to be less than $50^{th}$ cycle number using various S-shaped functions, such as logistic function, Gompertz function, and Chapman function. Therefore, the samples were all determined to be positive.

Example 4: Detection of Target Analyte Using S-Shaped Function for Slope Data Set with Additional Data Points (Embodiment 4)

The selected portion of the slope data set as determined to have a slope value equal to or greater than the filtering threshold in Example 1 was added with additional data points having the same slope values as the slope value at the end cycle number of the selected portion. Then, an S-shaped function that approximates the selected portion with additional data points was calculated. Finally, the FDM cycle number as a Ct value was determined from the S-shaped function to detect a target analyte as described in Example 2.

Figure 8:
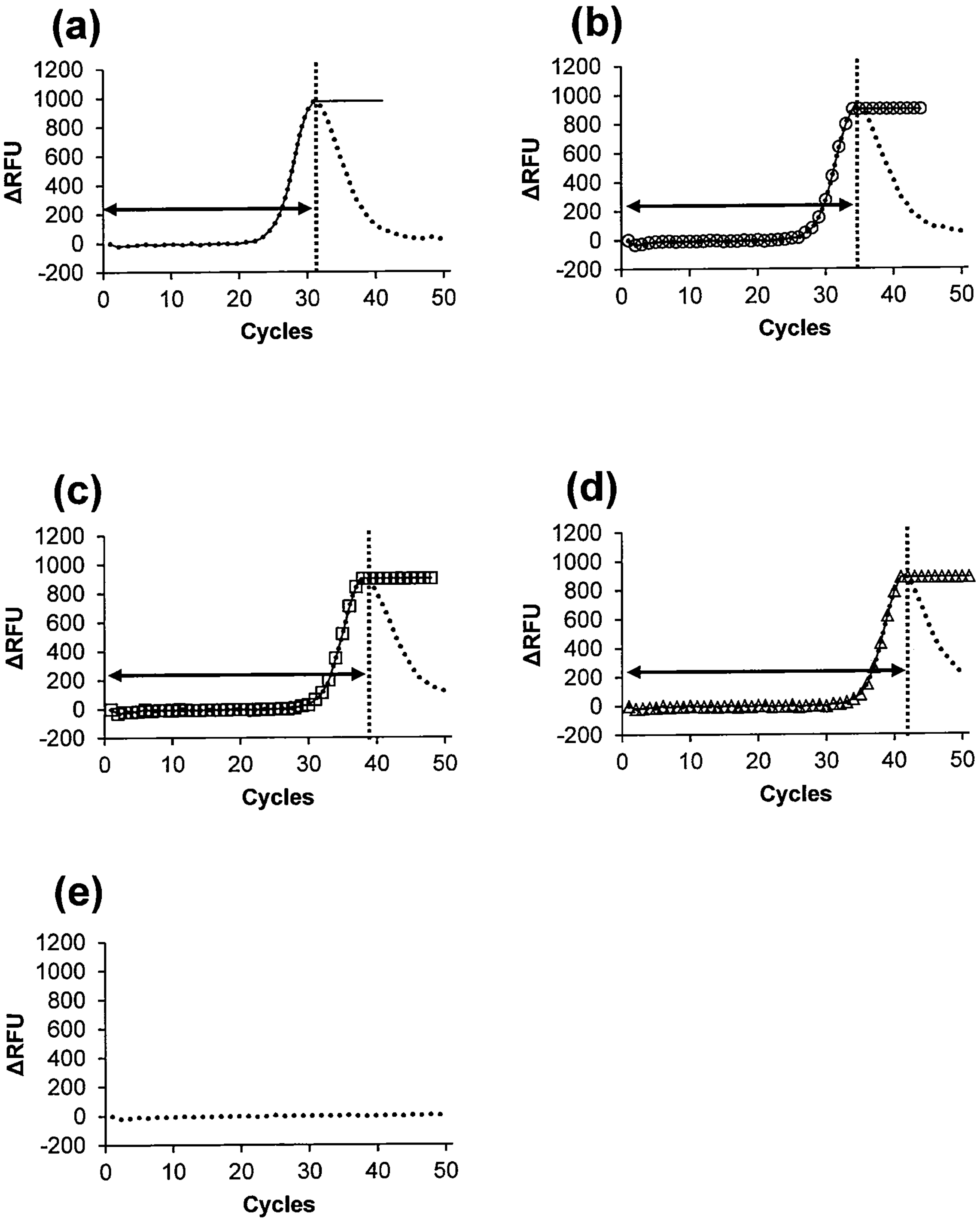
FIG. 8 shows five slope data sets in which additional ten (10) data points are added after the end cycle of a selected portion ((a): NG 100 pg; (b): NG 10 pg; (c): NG 1 pg; (d): NG 100 fg and (e): NTC).

Specifically, additional ten (10) data points having slope values equal to the slope value at the end cycle of the selected portion were added after the end cycle, as depicted in FIG. 8 ((a): NG 100 pg; (b): NG 10 pg; (c): NG 1 pg; (d): NG 100 fg and (e): NTC).

For a slope data set as depicted in graph (a) of FIG. 5, a portion ranging from $1^{st}$ to $31^{st}$ cycle numbers was selected. Then, additional ten (10) data points having the same values as the slope value at the $31^{st}$ cycle number were added immediately after the $31^{st}$ cycle number, i.e., at $32^{nd}$ to $41^{st}$ cycle numbers.

Similarly, the selected portions as depicted in graphs (b), (c) and (d) of FIG. 5 were added with additional data points at positions of $35^{th}$ to $44^{th}$ cycle numbers, $39^{th}$ to $48^{th}$ cycle numbers, and $42^{nd}$ to $51^{st}$ cycle numbers, respectively.

Figure 9:
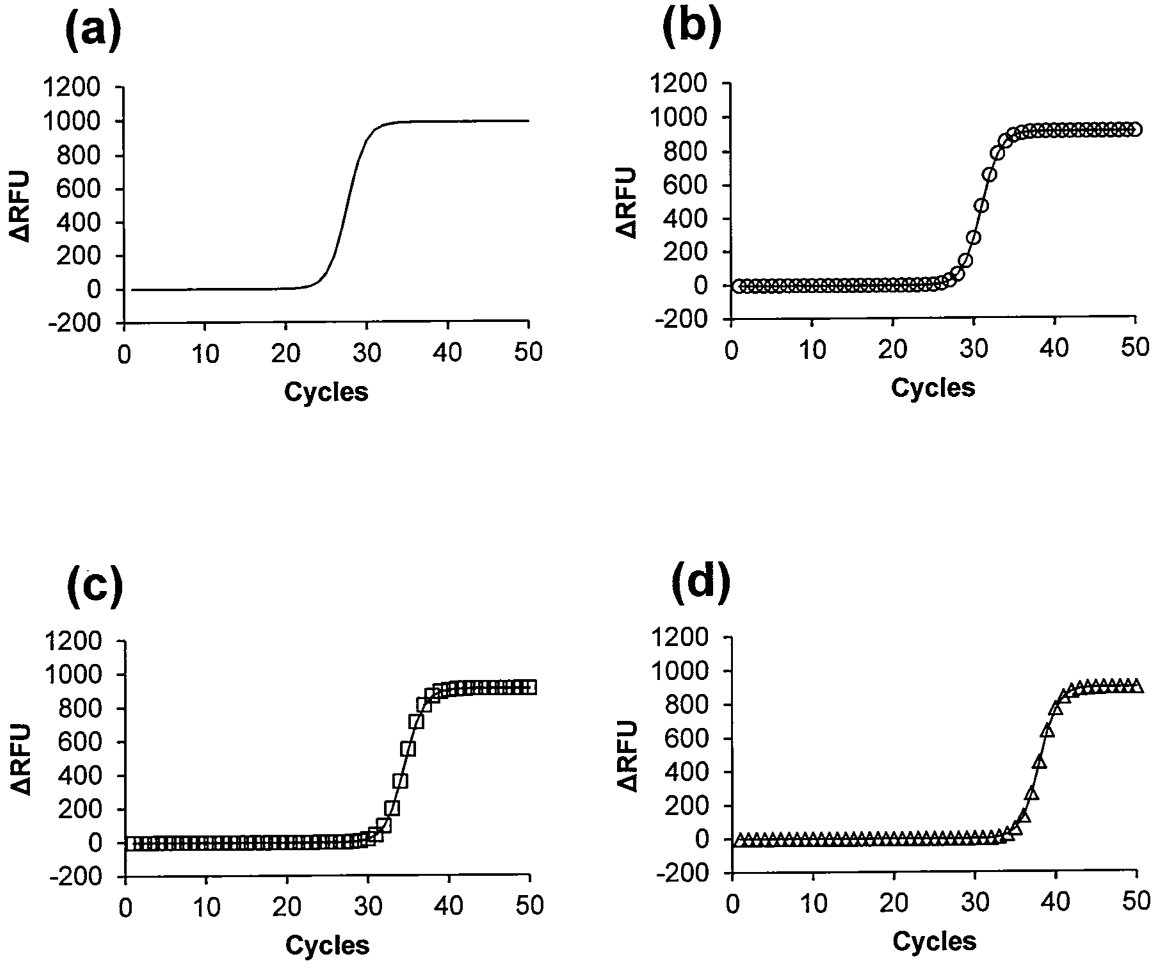
FIG. 9 shows four curves produced by the sigmoid function that approximates each of the selected portions having the additional data points for samples containing genomic DNA of *Neisseria gonorrhoeae* (NG) at various concentrations as a target analyte ((a): NG 100 pg; (b): NG 10 pg; (c): NG 1 pg; and (d): Ng 100 fg).

The selected portions having the additional data points added were fitted to a sigmoid function. The resulting five curves produced by the sigmoid function for various concentrations of target analytes are depicted in FIG. 9 ((a): NG 100 pg; (b): NG 10 pg; (c): NG 1 pg; and (d): NG 100 fg), and the parameter values for each sigmoid function are shown in Table 9 below.

TABLE 9

| parameter | Parameter value | | | |
|---|---|---|---|---|
| | 100 pg | 10 pg | 1 pg | 100 fg |
| $\alpha_1$ | −3 | −5 | −3 | −1 |
| $\alpha_2$ | 987 | 909 | 909 | 896 |
| $\alpha_3$ | 27.59 | 30.93 | 34.50 | 37.97 |
| $\alpha_4$ | 0.380 | 0.379 | 0.368 | 0.368 |

Then, a sample whose FDM cycle number ($\alpha_3$) is larger than the $50^{th}$ cycle was determined to be negative.

The results are shown in Table 10 below.

TABLE 10

| | Target analyte | | | | |
|---|---|---|---|---|---|
| | Positive | | | | Negative |
| Concentration | 100 pg | 10 pg | 1 pg | 100 fg | — |
| FDM cycle number | 27.59 | 30.93 | 34.50 | 37.97 | — |
| Result | Positive | Positive | Positive | Positive | Negative |

As shown in Table 10, the samples containing various concentrations of target analytes were found to have the FDM cycle number ($\alpha_3$) of 27.59, 30.93, 34.50, and 37.97, respectively. Therefore, the samples were all determined to be positive, due to the FDM cycle numbers of less than 50.

Comparative Example 1: Detection of Target Analyte Using Raw Data Set

The procedure of Example 1 was repeated except for using the entire of a raw data set in place of using a selected portion of the slope data set.

Each raw data set was subjected to baselining before calculating an S-shaped function from the raw data set, and then filtered out using a filtering threshold 200. Then, the sigmoid function was calculated which approximates the raw data set.

Figure 10:
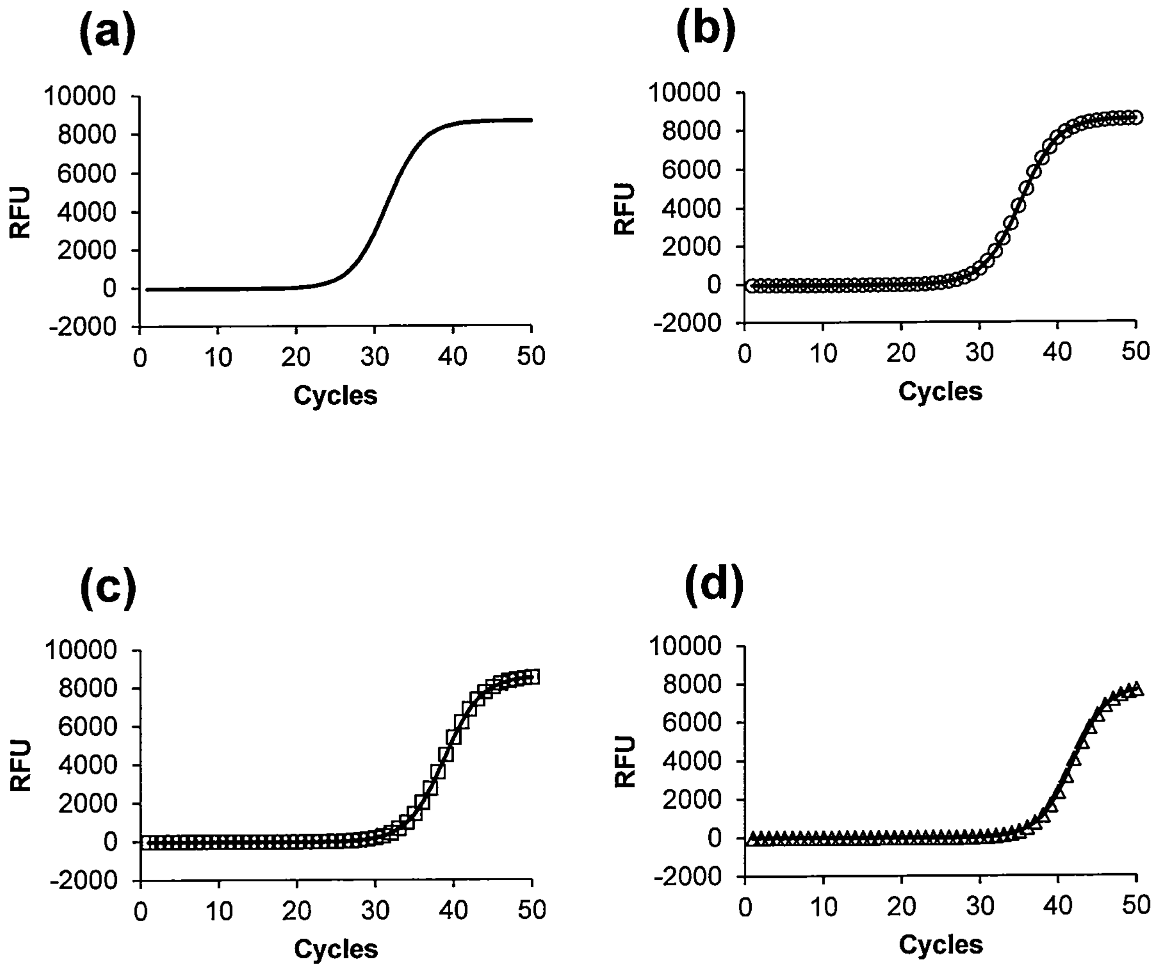
FIG. 10 shows four curves produced by the sigmoid function that approximates each of the raw data sets for samples containing genomic DNA of *Neisseria gonorrhoeae* (NG) at various concentrations as a target analyte in accordance with the method of Comparative Example 1 ((a): NG 100 pg; (b): NG 10 pg; (c): NG 1 pg; (d): 100 fg).

The resulting four curves produced by the sigmoid functions fitted to the raw data sets for the samples containing various concentrations of *Neisseria gonorrhoeae* (NG) genomic DNA as the target analyte are depicted in FIG. 10 ((a): NG 100 pg; (b): NG 10 pg; (c): NG 1 pg; and (d): NG 100 fg), and the parameter values for each sigmoid function are shown in Table 11 below.

TABLE 11

| Parameter | Parameter value | | | |
|---|---|---|---|---|
| | NG 100 pg | NG 10 pg | NG 1 pg | NG 100 fg |
| $\alpha_1$ | −47 | −46 | −36 | −23 |
| $\alpha_2$ | 8660 | 8591 | 8574 | 7827 |
| $\alpha_3$ | 31.53 | 35.22 | 38.77 | 41.84 |
| $\alpha_4$ | 0.193 | 0.184 | 0.185 | 0.200 |

A detection threshold was applied to each of the curves produced by the sigmoid functions to determine as a Ct value the intersection between each of the curves and the threshold. The detection threshold was set to 800, which corresponds to approximately 10% of $\alpha_2$ values for the sigmoid functions.

Thereafter, a sample having a slope value above the detection threshold, i.e., a sample having a Ct value, was determined to be positive, while a sample having all slope values below the detection threshold, i.e., a sample having no Ct value, was determined to be negative.

The results are shown in Table 12 below.

TABLE 12

| | Target analyte | | | | |
|---|---|---|---|---|---|
| | Positive | | | | Negative |
| Concentration | 100 pg | 10 pg | 1 pg | 100 fg | — |
| Filtering threshold | | | 200 | | |
| Maximum signal value | 8845 | 8804 | 8741 | 7869 | 99 |
| Proceed to next step | Yes | Yes | Yes | Yes | No |
| Detection threshold | | | 800 | | |
| Ct value | 26.48 | 29.98 | 33.48 | 37.16 | — |
| Result | positive | positive | positive | positive | negative |

As shown in Table 12, the samples containing various concentrations of target analytes were found to have the Ct value of 26.48, 29.98, 33.48, and 37.16, respectively. Therefore, the samples were all determined to be positive.

Comparative Example 2: Detection of Target Analyte Using Raw Data Set

The procedure of Example 2 was repeated except for using the entire of a raw data set as a whole in place of using a selected portion of the slope data set.

The FDM cycle numbers were determined from the sigmoid functions calculated in Comparative Example 1.

Then, a sample whose FDM cycle number ($\alpha_3$) is less than or equal to the end cycle number of the data set, e.g., 50, was determined to be positive, while a sample whose FDM cycle number is greater than the end cycle number was determined to be negative.

The results are shown in Table 13 below.

TABLE 13

| | Target analyte | | | | |
|---|---|---|---|---|---|
| | Positive | | | | Negative |
| Concentration | 100 pg | 10 pg | 1 pg | 100 fg | — |
| Filtering threshold | | | 200 | | |
| Maximum slope value | 8845 | 8804 | 8741 | 7869 | 99 |
| Proceed to next step | Yes | Yes | Yes | Yes | No |
| FDM cycle number | 31.53 | 35.22 | 38.77 | 41.84 | — |
| Result | Positive | Positive | Positive | Positive | Negative |

As shown in Table 13, the samples containing various concentrations of target analytes were found to have the FDM cycle number ($\alpha_3$) of 31.53, 35.22, 38.77, and 41.84, respectively. Thus, the samples were determined to be positive as the FDM cycle numbers were all less than 50.

The results of Examples 1 and 2 (present methods) and Comparative Examples 1 and 2 (conventional methods) are summarized in Table 14 below.

TABLE 14

| | | Target analyte | | | | |
|---|---|---|---|---|---|---|
| | Concen- | positive | | | | negative |
| Method | tration | 100 pg | 10 pg | 1 pg | 100 fg | — |
| Example 1 | Ct value | 24.87 | 28.27 | 31.81 | 35.31 | — |
| | Result | Positive | Positive | Positive | Positive | negative |
| Example 2 | Ct value | 27.92 | 31.40 | 34.85 | 38.44 | — |
| | Result | Positive | Positive | Positive | Positive | negative |
| Comparative | Ct value | 26.48 | 29.98 | 33.48 | 37.16 | — |
| Example 1 | Result | Positive | positive | Positive | Positive e | negative |
| Comparative | Ct value | 31.53 | 35.22 | 38.77 | 41.84 | — |
| Example 2 | Result | Positive | Positive | Positive | Positive | negative |

As shown in Table 14, it was found that the method of the present invention (Examples 1 and 2) using an S-shaped function for a selected portion of a slope data set can be used to detect the presence of the target analyte, which is comparable to the conventional method (Examples 3 and 4). In particular, using a parameter of the S-shaped function rather than using a detection threshold is expected to allow for more accurate detection of target analytes without being affected by signal variations between reactions or apparatuses.

In addition, the conventional method (Comparative Examples 1 and 2) using a best-fit S-shaped function to a raw data set requires a complicated baseline slope correction in order to increase the goodness of fit of the function, while the method of the present invention can rule out such baseline slope correction.

Example 5: Quantification of Target Analyte Using Slope Data Set

It was investigated whether the method of the present invention could be used to quantify a target analyte in a sample.

In this Example, the standard curve method was used for absolute quantification. Specifically, serial dilutions of a standard target analyte were subjected to a real-time PCR reaction to obtain a standard curve, from which the coefficient of determination ($R^2$) and PCR efficiency were calculated to confirm the applicability of the method of the present invention to quantification of target analytes. In this example, the FDM cycle numbers as determined in Example 2 were used.

<5-1> Obtaining a Standard Curve Using Standard Target Analytes

For absolute quantification of the target analyte, the standard curve was obtained as follows.

<5-1-1> Performing Real-Time PCR and Obtaining Raw Data Set

Figure 11:
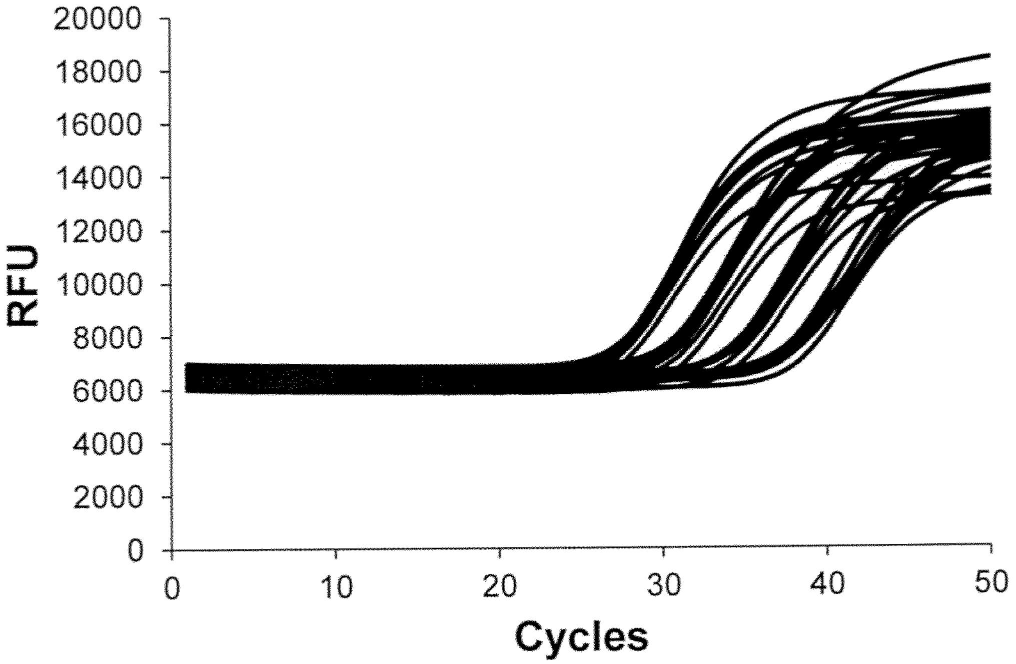
FIG. 11 shows raw data sets obtained from PCR reaction repeated ten times with samples containing genomic DNA of *Neisseria gonorrhoeae* (NG) at various concentrations as a target analyte.

The real-time PCR reaction was repeated ten times with four different concentrations of target analytes (*Neisseria gonorrhoeae* (NG) genomic DNA) as in Example <1-1>, thereby obtaining raw data sets. The resulting raw data sets are shown in FIG. 11.

<5-1-2> Obtaining Slope Data Set

The raw data sets were each converted to slope data sets as in Example <1-2>.

<5-1-3> Filtering Out Slope Data Set

A filtering threshold 100 was then applied to each of the slope data sets as in Example <1-3>. As a result, all slope data sets were found to have any slope value above the filtering threshold.

<5-1-4> Calculating S-Shaped Function for Selected Portion of Slope Data Set

As in Example <1-4>, a sigmoid function that approximates a selected portion of each of the slope data sets was calculated. The values of the parameters of each sigmoid function are shown in Table 15 below.

TABLE 15

| | Repeat | Selected | Parameter | | | |
|---|---|---|---|---|---|---|
| concentration | No. | portion | $\alpha_1$ | $\alpha_2$ | $\alpha_3$ | $\alpha_4$ |
| 100 pg | 1 | 1~31 cycles | −7 | 1028 | 27.97 | 0.326 |
| | 2 | 1~31 cycles | −2 | 1384 | 28.59 | 0.313 |
| | 3 | 1~31 cycles | −4 | 1213 | 27.88 | 0.336 |
| | 4 | 1~31 cycles | −5 | 1250 | 28.18 | 0.325 |
| | 5 | 1~31 cycles | −6 | 1229 | 28.01 | 0.330 |
| | 6 | 1~31 cycles | −5 | 1170 | 27.85 | 0.326 |
| | 7 | 1~31 cycles | −8 | 1196 | 27.99 | 0.331 |
| | 8 | 1~31 cycles | −8 | 1151 | 27.82 | 0.328 |
| | 9 | 1~31 cycles | −9 | 1166 | 28.11 | 0.318 |
| | 10 | 1~31 cycles | −5 | 1092 | 27.92 | 0.322 |
| 10 pg | 1 | 1~34 cycles | −6 | 1041 | 31.57 | 0.315 |
| | 2 | 1~34 cycles | −4 | 1215 | 31.62 | 0.319 |
| | 3 | 1~35 cycles | −8 | 1226 | 31.63 | 0.332 |
| | 4 | 1~34 cycles | −6 | 1138 | 31.42 | 0.325 |
| | 5 | 1~34 cycles | −6 | 1261 | 31.31 | 0.311 |
| | 6 | 1~34 cycles | −7 | 1243 | 31.43 | 0.319 |
| | 7 | 1~35 cycles | −5 | 1109 | 31.00 | 0.352 |
| | 8 | 1~35 cycles | −5 | 1153 | 31.41 | 0.345 |
| | 9 | 1~34 cycles | −5 | 1168 | 31.34 | 0.322 |
| | 10 | 1~34 cycles | −8 | 1051 | 31.40 | 0.307 |
| 1 pg | 1 | 1~38 cycles | −5 | 1016 | 35.17 | 0.328 |
| | 2 | 1~39 cycles | −3 | 1003 | 34.98 | 0.311 |
| | 3 | 1~38 cycles | −7 | 1203 | 35.00 | 0.328 |
| | 4 | 1~39 cycles | −6 | 984 | 34.75 | 0.317 |
| | 5 | 1~38 cycles | −7 | 1175 | 35.09 | 0.320 |
| | 6 | 1~38 cycles | −4 | 1157 | 34.83 | 0.322 |
| | 7 | 1~39 cycles | −8 | 941 | 34.58 | 0.316 |
| | 8 | 1~38 cycles | −6 | 1181 | 34.89 | 0.330 |
| | 9 | 1~39 cycles | −7 | 940 | 34.37 | 0.324 |
| | 10 | 1~38 cycles | −5 | 1008 | 34.85 | 0.312 |
| 100 fg | 1 | 1~42 cycles | −4 | 1012 | 38.67 | 0.338 |
| | 2 | 1~42 cycles | −3 | 1100 | 39.00 | 0.267 |
| | 3 | 1~41 cycles | −7 | 1197 | 38.26 | 0.321 |
| | 4 | 1~42 cycles | −6 | 1020 | 38.83 | 0.267 |
| | 5 | 1~42 cycles | −5 | 1056 | 38.37 | 0.344 |
| | 6 | 1~41 cycles | −5 | 1167 | 38.12 | 0.327 |
| | 7 | 1~42 cycles | −7 | 977 | 38.09 | 0.268 |
| | 8 | 1~42 cycles | −4 | 1121 | 38.57 | 0.339 |
| | 9 | 1~42 cycles | −8 | 972 | 38.51 | 0.261 |
| | 10 | 1~41 cycles | −3 | 1035 | 38.44 | 0.313 |

<5-1-5> Generation of Standard Curve

The FDM cycle numbers were determined from the sigmoid functions as in Example 2. Then, a standard curve for absolute quantification was generated by plotting the log transformed concentration (x-axis) of the standard target analyte vs the FDM (y-axis).

Figure 12:
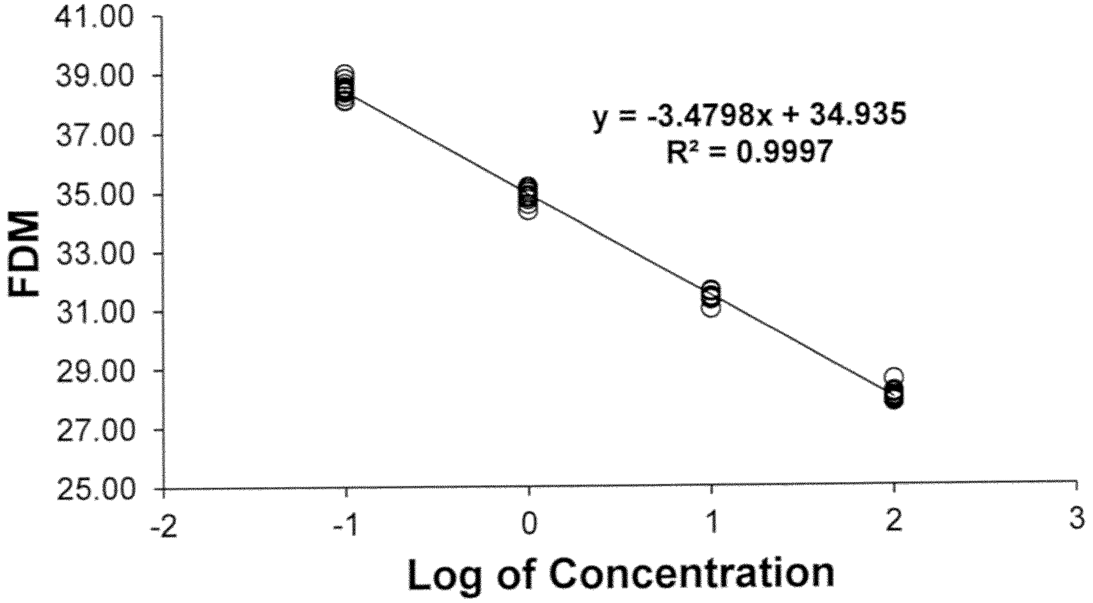
FIG. 12 shows a standard curve generated using samples containing four concentrations of target analytes. The standard curve represents the relationship between the log transformed concentration of the target analyte and the first derivative maximum (FDM).

The standard curve generated is shown in FIG. 12, and the coefficient of determination ($R^2$) and PCR efficiency of the standard curve are shown in Table 16 below.

TABLE 16

| | Standard curve | | | |
|---|---|---|---|---|
| Repeat No. | Equation for standard curve | $R^2$ | PCR efficiency | PCR efficiency (%) |
| 1 | y = −3.571x + 35.131 | 0.9999 | 1.905 | 91% |
| 2 | y = −3.460x + 35.277 | 0.9959 | 1.945 | 95% |
| 3 | y = −3.451x + 34.914 | 0.9989 | 1.949 | 95% |
| 4 | y = −3.529x + 35.059 | 0.9968 | 1.920 | 92% |
| 5 | y = −3.487x + 34.936 | 0.9992 | 1.935 | 94% |
| 6 | y = −3.422x + 34.769 | 0.9996 | 1.960 | 96% |
| 7 | y = −3.389x + 34.610 | 0.9986 | 1.973 | 97% |
| 8 | y = −3.570x + 34.957 | 0.9999 | 1.906 | 91% |
| 9 | y = −3.421x + 34.793 | 0.9950 | 1.960 | 96% |
| 10 | y = −3.499x + 34.903 | 0.9999 | 1.931 | 93% |
| Average | y = −3.480x + 34.935 | 0.9997 | 1.938 | 94% |

As shown in Table 16, the average $R^2$ value of the standard curves was 0.9997, and the average PCR efficiency was 94%.

<5-2> Evaluation of Applicability to Quantification

The applicability of the method of the present invention to quantification of target analytes was evaluated based on the $R^2$ value and PCR efficiency.

The hallmarks of an optimized quantitative PCR (qPCR) assay are: Linear standard curve ($R^2$>0.98) and high amplification efficiency (90-105%) (See, 2006 Bio-Rad Laboratories, Inc. Real-Time PCR Applications Guide).

As shown in Table 16, the minimum $R^2$ of the standard curves obtained by the method of the present invention was 0.995, and the PCR amplification efficiencies were within 90~105%, all of which meet the criteria.

The results demonstrate that the method of the present invention using an S-shaped function fitted to a selected portion of a slope data set is applicable to quantification of a target analyte.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target analyte in a sample, comprising the steps of:

(a) performing, by a real-time amplification instrument, a real-time amplification reaction for a target analyte to obtain a first data set representing a real-time amplification curve for a target analyte; wherein said first data set includes a plurality of data points, each having a cycle number and a signal value at the cycle number;

(b) transforming, by a processor operatively connected to the amplification instrument, a signal value at each cycle number in the first data set into a slope value at each cycle number to obtain a second data set; wherein said second data set includes a plurality of data points, each having a cycle number and a slope value at the cycle number;

(c) transforming, by a processor, the second data set into an S-shaped function by approximating the S-shaped function using a selected portion of the second data set; wherein the selected portion ranges from a first cycle number to a cycle number having a maximum slope value in the second data set; wherein the S-shaped function is any one selected from the group consisting of a sigmoid function, a logistic function, a Gompertz function, and a Chapman function; and (d) determining, by a processor, a threshold cycle (Ct) value from the S-shaped function, determining the presence or absence of the target analyte in the sample based on the Ct value, and outputting the determination result through a display or data storage device of the amplification instrument.

2. The method of claim 1, wherein the first data set is a raw data set, a mathematically modified data set of the raw data set, a normalized data set of the raw data set, or a normalized data set of the mathematically modified data set.

3. The method of claim 1, wherein the slope value is obtained by a differentiation, a difference, a difference quotient, a ratio, or linear regression of the signal values.

4. The method of claim 1, wherein the selected portion of the second data set comprises at least 5 cycles.

5. The method of claim 1, wherein the approximation of an S-shaped function in step (c) comprises determining parameters for the S-shaped function.

6. The method of claim 1, wherein the S-shaped function is represented by any one of Equations II-IV:

$$f(x) = \alpha_1 + \frac{\alpha_2 - \alpha_1}{1 + 10^{\alpha_4(\alpha_3 - x)}} \quad \text{Equation II}$$

$$f(x) = \alpha_1 + \frac{\alpha_2 - \alpha_1}{1 + (x/\alpha_3)^{\alpha_4}} \quad \text{Equation III}$$

$$f(x) = \alpha_1 + (\alpha_2 - \alpha_1)10^{-e^{(\alpha_3 - x)/\alpha_4}} \quad \text{Equation IV}$$

$$f(x) = \alpha_1 + (\alpha_2 - \alpha_1)(1 - 10^{-\alpha_4 x})^c \quad \text{Equation V}$$

wherein $\alpha_1$, $\alpha_2$, $\alpha_3$, and $\alpha_4$ are parameters as determined by fitting of the S-shaped function to the selected portion of the slope data set, and x is a cycle number.

7. The method of claim 1, wherein determining a threshold cycle (Ct) value from the S-shaped function comprises (i) calculating a first, second, or $n^{th}$ order derivative of the S-shaped function, wherein n is a natural number; and (ii) determining a cycle number having a maximum of the first, second or $n^{th}$ derivative as a threshold cycle (Ct) value.

8. The method of claim 1, wherein determining a threshold cycle (Ct) value in step (d) is performed using one or more parameters of the S-shaped function.

9. The method of claim 1, further comprising the following steps between step (a) and step (b):

(a1) applying a threshold value to the first data set; and (a2) proceeding to the next step (b), if the first data set has a signal value exceeding the threshold value.

10. The method of claim 1, further comprising the following steps between step (b) and step (c):

(b1) applying a threshold value to the second data set; and (b2) proceeding to the next step (c), if the second data set has a slope value exceeding the threshold value.

11. The method of claim 1, wherein the target analyte is a target nucleic acid molecule.

12. The method of claim 1, wherein the selected portion of the second data set further comprises one or more additional data points after the end cycle of the selected portion, the one or more additional data points having a slope value equal to the slope value at the end cycle number of the selected portion.

13. A non-transitory computer readable storage medium containing instructions to configure a processor to perform a method for detecting a target analyte in a sample, the method comprising:

(a) receiving a first data set representing a real-time amplification curve by a real-time amplification reaction for a target analyte; wherein said first data set includes a plurality of data points, each having a cycle number and a signal value at the cycle number;

(b) transforming a signal value at each cycle number in the first data set into a slope value at each cycle number to obtain a second data set; wherein said second data set includes a plurality of data points, each having a cycle number and a slope value at the cycle number;

(c) transforming the second data set into an S-shaped function by approximating the S-shaped function using a selected portion of the second data set; wherein the selected portion ranges from a first cycle number to a cycle number having a maximum slope value in the second data set; wherein the S-shaped function is any one selected from the group consisting of a sigmoid function, a logistic function, a Gompertz function, and a Chapman function; and (d) determining a threshold cycle (Ct) value from the S-shaped function, determining the presence or absence of the target analyte in the sample based on the Ct value, and outputting the determination result through a display or data storage device of the amplification instrument.

14. A device for detecting a target analyte in a sample, comprising: (a) a computer processor, and (b) the computer readable storage medium of claim 13.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic nucleotide: NG_F

<400> SEQUENCE: 1

tacgcctgct actttcacgc t                                      21
```

-continued

<210> SEQ ID NO 2
<211> LENGTH: 21
<212> TYPE: DNA
<213> ORGANISM: Artificial Sequence
<220> FEATURE:
<223> OTHER INFORMATION: Synthetic nucleotide: NG_R

<400> SEQUENCE: 2
caatggatcg gtatcactcg c 21

<210> SEQ ID NO 3
<211> LENGTH: 22
<212> TYPE: DNA
<213> ORGANISM: Artificial Sequence
<220> FEATURE:
<223> OTHER INFORMATION: Synthetic nucleotide: NG_P

<400> SEQUENCE: 3
tgcccctcat tggcgtgttt cg 22